United States Patent
Hollaus

(10) Patent No.: US 12,428,499 B2
(45) Date of Patent: Sep. 30, 2025

(54) THIOL-MODIFIED HYALURONAN AND HYDROGEL COMPRISING THE CROSSLINKED HYALURONAN

(71) Applicant: CROMA-PHARMA GMBH, Leobendorf (AT)

(72) Inventor: Ralph Hollaus, Wein (AT)

(73) Assignee: CROMA-PHARMA GMBH, Leobendorf (AT)

( * ) Notice: Subject to any disclaimer, the term of this patent is extended or adjusted under 35 U.S.C. 154(b) by 813 days.

(21) Appl. No.: 17/776,154

(22) PCT Filed: Dec. 18, 2020

(86) PCT No.: PCT/EP2020/087140
§ 371 (c)(1),
(2) Date: May 11, 2022

(87) PCT Pub. No.: WO2021/123247
PCT Pub. Date: Jun. 24, 2021

(65) Prior Publication Data
US 2022/0403054 A1    Dec. 22, 2022

(30) Foreign Application Priority Data
Dec. 19, 2019 (EP) .................................. 19218338

(51) Int. Cl.
*C08B 37/08* (2006.01)
*A61L 27/20* (2006.01)
*A61L 27/52* (2006.01)

(52) U.S. Cl.
CPC .......... *C08B 37/0072* (2013.01); *A61L 27/20* (2013.01); *A61L 27/52* (2013.01)

(58) Field of Classification Search
CPC ....... C08B 37/0072; A61L 27/20; A61L 27/52
See application file for complete search history.

(56) References Cited

U.S. PATENT DOCUMENTS

| | | | |
|---|---|---|---|
| 6,884,788 | B2 | 4/2005 | Bulpitt et al. |
| 2002/0071855 | A1 | 6/2002 | Sadozai et al. |
| 2008/0025950 | A1 | 1/2008 | Prestwich et al. |
| 2008/0221062 | A1 | 9/2008 | Miyamoto et al. |
| 2008/0292703 | A1 | 11/2008 | Renier et al. |
| 2009/0269417 | A1 | 10/2009 | Gonzalez et al. |
| 2012/0034271 | A1 | 2/2012 | Shu |
| 2013/0123210 | A1 | 5/2013 | Liu et al. |
| 2013/0210760 | A1 | 8/2013 | Liu et al. |
| 2016/0220729 | A1 | 8/2016 | Gousse et al. |
| 2019/0270829 | A1 | 9/2019 | Zeng et al. |

FOREIGN PATENT DOCUMENTS

| | | | |
|---|---|---|---|
| CA | 2348842 | A1 | 5/2000 |
| CN | 101367884 | A | 2/2009 |
| CN | 101622017 | A | 1/2010 |
| CN | 101721349 | A | 6/2010 |
| CN | 102399295 | A | 4/2012 |
| CN | 104892962 | A | 9/2015 |
| CN | 107412002 | A | 12/2017 |
| EP | 0587715 | A1 | 3/1994 |
| EP | 1115433 | B1 | 12/2004 |
| EP | 1790665 | A1 | 5/2007 |
| EP | 2103631 | A1 | 9/2009 |
| EP | 2614828 | A2 | 7/2013 |
| WO | 92/20349 | A1 | 11/1992 |
| WO | 03/80135 | A1 | 10/2003 |
| WO | 2004/037164 | A2 | 5/2004 |
| WO | 2005/056608 | A1 | 6/2005 |
| WO | 2008/008857 | A2 | 1/2008 |
| WO | 2008/077172 | A2 | 7/2008 |
| WO | 2009/005790 | A2 | 1/2009 |
| WO | 2009/108100 | A1 | 9/2009 |
| WO | 2012/167079 | A2 | 12/2012 |
| WO | 2013/086024 | A2 | 6/2013 |
| WO | 2014/064632 | A1 | 5/2014 |
| WO | 2014/181147 | A1 | 11/2014 |
| WO | 2016/005785 | A1 | 1/2016 |
| WO | 2018/083326 | A1 | 5/2018 |
| WO | 2019/238954 | A1 | 12/2019 |

OTHER PUBLICATIONS

English translation of CN101367884A. Obtained from Espacenet on May 16, 2025 (Year: 2025).*
Serban, M. A, G. Yang and G.D. Prestwich (2008). "Synthesis, characterization and chondroprotective properties of a hyaluronan thioethyl ether derivative." Biomaterials 29(10): 1388-1399.
Shu et al., "Disulfide cross-linked hyaluronan hydrogels", Biomacromolecules, vol. 3, No. 6, 2002, pp. 1304-1311.
Shu et al., "Synthesis and evaluation of injectable, in situ crosslinkable synthetic extracellular matrices for tissue engineering", Journal of Biomedical Materials Research Part A, Dec. 15, 2006, pp. 902-912.
Shu, X. Z., S. Ahmad, Y. Liu, and G. D. Prestwich (2006). "Synthesis and evaluation of injectable, in situ crosslinkable synthetic extracellular matrices for tissue engineering." J Biomed Mater Res A 79(4):902-12.
Shu, X. Z., Y. Liu, F. Palumbo and G.D. Prestwich (2003). "Disulfide-crosslinked hyaluronan-gelatin hydrogel films: a covalent mimic of the extracellular matrix for in vitro cell growth." Biomaterials 24(21): 3825-3834.
Shu, X. Z., Y. Liu, Y. Luo, M. C. Roberts and G.D. Prestwich (2002). "Disulfide cross-linked hyaluronan hydrogels." Biomacromolecules 3(6): 1304-1311.

(Continued)

*Primary Examiner* — Scarlett Y Goon
*Assistant Examiner* — David H Cho
(74) *Attorney, Agent, or Firm* — Workman Nydegger

(57) ABSTRACT

A thiol-modified hyaluronan, wherein the thiol-modified hyaluronan comprises a plurality of modification groups with a thiol-group in the hyaluronan side-chains, wherein the modification group comprises an amino acid residue with basic side chain and a conjugated terminal naturally occurring amino-thiol as well as a sterile hydrogel composition comprising a crosslinked polymer, wherein the crosslinked polymer is an oxidation product of the thiol-modified hyaluronan and uses of the composition.

21 Claims, No Drawings

(56) References Cited

OTHER PUBLICATIONS

Sparer, R. V., N. Ekwuribe and A G. Walton (1983). Controlled Release from Glycosaminoglycan Drug Complexes. Controlled Release Delivery Systems. T. J. Roseman and S. Z. Mansdorf New York and Basel, Marcel Dekker, Inc.

Stern et al., "The many ways to cleave hyaluronan", Biotechnology Advances, vol. 25, No. 6, 2007, pp. 537-557.

Stocks D. et al, "Rheological Evaluation of the Physical Properties of Hyaluronic Acid Dermal Fillers," J Drugs Dermatol, vol. 10, Issue 9, 2011, pp. 974-980.

Stocks et al., "Rheological evaluation of the physical properties of hyaluronic acid dermal fillers", J. Drugs Dermatol., vol. 10, No. 9, 2011, pp. 974-980.

The international gharmacogoeia [electronic resource]—9th ed. (2019). Methods of sterilization. Geneva, World Health Organization.

The international pharmacogoeia [electronic resource]—9th ed. (2019). Methods of sterilization. Geneva, World Health Organization.

Tokita et al., "Degradation of hyaluronic acid-Kinetic study and thermodynamics", Eur. Polym. J., vol. 32, No. 8, 1996, pp. 1011-1014.

Troncoso et al., "A kinetic study of the degradation of hyaluronic acid at high concentrations of sodium hydroxide", student thesis, 2016.

Agerup, B., P. Berg and C. Akermark (2005). "Non-Animal Stabilized Hyaluronic Acid." BioDrugs 19(1): 23-30.

Aufort et al., "Oxorhenium-Mediated Assembly of Noncyclic Selective Integrin Antagonists: A Combinatorial Approach", ChemBioChem, vol. 12, Issue 4, 2011, pp. 583-592.

Bae, H. D., L. J. Yanke, K. J. Cheng and L.B. Selinger (1999). "A novel staining method for detecting phytase activity." J Microbiol Methods 39(1): 17-22.

Beasley, K. L., M.A. Weiss, R. A. Weiss (2009). "Hyaluronic acid fillers: a comprehensive review." Facial Plast Surg 25:86-94.

Bernkop-Schnurch, A (2005). "Thiomers: a new generation of mucoadhesive polymers." Adv Drug Deliv Rev 57(11): 1569-1582.

Bernkop-Schnurch, A and T. E. Hopf (2001). "Synthesis and in Vitro Evaluation of Chitosan-Thioglycolic Acid Conjugates." Scientia Pharmazeutica 69: 109-118.

Bernkop-Schnurch, A, C. E. Kast and M. F. Richter (2001). "Improvement in the mucoadhesive properties of alginate by the covalent attachment of cysteine." J Control Release 71(3): 277-285.

Bernkop-Schnurch, A, V. Schwarz and S. Steininger (1999). "Polymers with thiol groups: a new generation of mucoadhesive polymers?" Pharm Res 16(6): 876-881.

Bernuzzi et al., "An innovative way to thermally sterilize hyaluronic acid pre-filled syringes", 2016 white paper available under https://demo6.esoul.it/wp-content/uploads/2019/07/WP_Thermal_Sterilization_PFS_with_Hyaluronic_Acid.pdf.

Borke et al., "Optimized triazine-mediated amidation for efficient and controlled functionalization of hyaluronic acid", Carbohydrate Polymers, vol. 116, 2015, pp. 42-50.

Bothner, H., T. Waaler and O. Wik (1988). "Limiting viscosity number and weight average molecular weight of hyaluronate samples produced by heat degradation." International Journal of Biological Macromolecules 10(5): 287-291.

Boulle et al., "A review of the metabolism of 1,4-butanediol diglycidyl ether-crosslinked hyaluronic acid dermal fillers", Dermatol. Surg., vol. 39, No. 12, 2013, pp. 1758-1766.

Choi et al., "Modulation of biomechanical properties of hyaluronic acid hydrogels by crosslinking agents", J. Biomed. Mater Res. Part A, vol. 103, No. 9, 2015, pp. 3072-3080.

Choi, J.-i., J.-K. Kim, J.-H. Kim, D.-K. Kweon and J.-W. Lee (2010). "Degradation of hyaluronic acid powder by electron beam irradiation, gamma ray irradiation, microwave irradiation and thermal treatment: A comparative study." Carbohydrate Polymers 79(4): 1080-1085.

Cowman et al., "Improved agarose gel electrophoresis method and molecular mass calculation for high molecular mass hyaluronan, Analytical Biochemistry", vol. 417, No. 1, 2011, pp. 50-56.

Cowman M.K. et al, "Improved agarose gel electrophoresis method and molecular mass calculation for high molecular mass hyaluronan," Analytical Biochemistry, vol. 417, 2011, pp. 50-56.

Edsman, K., A. Ohrlund, C. Sturesson, L. Nord, A.H. Kenne and J. Nasstrom (2010). The Difference Between Stabilization and Crosslinking. 8th Anti-aging Medicine World Congress (AMWC). Monaco.

Gatta et al., "Biophysical and biological characterization of a new line of hyaluronan-based dermal fillers: A scientific rationale to specific clinical indications", Materials Science and Engineering C, vol. 68, 2016, pp. 565-572.

Griesser et al., "Thiolated Hyaluronic Acid as Versatile Mucoadhesive Polymer: From the Chemistry Behind to Product Developments—What Are the Capabilities?", Polymers, vol. 10, No. 3, 2018, 16 Pages.

Hoet et al., "Polyamines in the lung: polyamine uptake and polyamine-linked pathological or toxicological conditions", Am. J. Physiol. Lung Cell. Mol. Physiol., vol. 278, No. 3, 2000, pp. L417-L433.

Hoet P. H.M. et al, "Polyamines in the lung: polyamine uptake and polyamine-linked pathological or toxicological conditions," Am. J. Physiol. Lung Cell. Mol. Physiol, vol. 278, 2000, pp. L417-L433.

International Preliminary Report on Patentability received for PCT Patent Application No. PCT/EP2019/065754, mailed on Dec. 24, 2020, 7 pages.

International Search Report and Written Opinion received for PCT Patent Application No. PCT/EP2020/087140, mailed on Apr. 26, 2021, 11 pages.

International Search Report issued in PCT/EP2019/065754, dated Sep. 20, 2019.

International Search Report issued in PCT/EP2019/065755 mailed Sep. 19, 2019.

International Search Report issued in PCT/EP2019/065756 mailed Oct. 1, 2019.

Jones, D. S. (2009). Chitosan. Handbook of Pharmaceutical Excipients Sixth Edition. R. C. Rowe, P. J. Sheskey and M. E. Quinn. London Chicago, Pharmaceutical Press: 159-161.

Kafedjiiski, et al, "Synthesis and in vitro evaluation of thiolated hyaluronic acid for mucoadhesive drug delivery" International Journal of Pharmaceutics, Eslevier, NL vol. 343, No. 1-2, Aug. 30, 2007, pp. 48-58.

Kafedjiiski, et al., "Synthesis and in vitro evaluation of thiolated hyaluronic acid for mucoadhesive drug delivery", International Journal of Pharmaceutics, Elsevier, NL, Vo. 343, No. 1- 2, Aug. 30, 2007.

Kast, C. E. and A Bernkop-Schnurch (2001). "Thiolated polymers-thiomers: development and in vitro evaluation of chitosan-thioglycolic acid conjugates." Biomaterials 22(17): 2345-2352.

Kast, C. E. and A Bernkop-Schnurch (2002). "Polymer-cysteamine conjugates: new mucoadhesive excipients for drug delivery?" Int J Pharm 234(1-2): 91-99.

Krauland, A H., M. H. Hoffer and A Bernkop-Schnurch (2005). "Viscoelastic properties of a new in situ gelling thiolated chitosan conjugate." Drug Dev Ind Phann 31(9): 885-893.

La Gatta, A. et al., 2016, „Biophysical and biological characterization of a new line of hyaluronan-based dermal fillers: A scientific rationale to specific clinical indications, Materials Science and Engineering C 68: 565-572.

Liang et al., "Investigating triazine-based modification of hyaluronan using statistical designs", Carbohydrate Polymers, vol. 132, Issue 5, 2015, pp. 472-480.

Lim, "Hyaluronic acid filler injections with a 31-gauge insulin syringe, Australasian Journal of Dermatology", vol. 51, No. 1, 2010, pp. 74-75.

Liu, N., L. Shao, X. Xu, J. Chen, H. Song, Q. He, Z. Lin, L. Zhang and C. B. Underhill (2002). "Hyaluronan metabolism in rat tail skin following blockage of the lymphatic circulation." Lymphology 35(1): 15-22.

Liu, Y., X. Zheng Shu and G. D. Prestwich (2005). "Biocompatibility and stability of disulfide-crosslinked hyaluronan films." Biomaterials 26(23): 4737-4746.

(56) References Cited

OTHER PUBLICATIONS

Lowry, K. M. and E. M. Beavers (1994). "Thermal stability of sodium hyaluronate in aqueous solution." J Biomed Mater Res 28(10): 1239-1244.
Marschutz, M. K. and A Bernkop-Schnurch (2002). "Thiolated polymers: self-crosslinking properties of thiolated 450 kDa poly(acrylic acid) and their influence on mucoadhesion." European Journal of Pharmaceutical Sciences 15(4): 387-394.
Mason, C., P. Dunnhill (2008). "A brief definition of regenerative medicine." Regen Med 3(1):1-5.
May, B. C., A. T. Fafarman, S. B. Hong, M. Rogers, L. W. Deady, S. B. Prusiner and F. E. Cohen (2003). "Potent inhibition of scrapie prion replication in cultured cells by bis-acridines." Proc Natl Acad Sci U S A 100(6): 3416-3421.
Monslow et al., "Hyaluronan—a functional and structural sweet spot in the tissue microenvironment," Frontiers in Immunology, vol. 6, No. 231, 2015, 19 Pages.
Naor, "Editorial: Interaction Between Hyaluronic Acid and Its Receptors (CD44, RHAMM) Regulates the Activity of Inflammation and Cancer, Frontiers in Immunology", vol. 7, No. 39, 2016, 4 Pages.
Palmberger, T. F., K. Albrecht, B. Loretz and A Bernkop-Schnurch (2007). "Thiolated polymers: Evaluation of the influence of the amount of covalently attached 1-cysteine to poly(acrylic acid)." European Journal of Pharmaceutics and Biopharmaceutics 66(3): 405-412.
Peppas, N. A (1991). "Physiologically Responsive Hydrogels." Journal of Bioactive and Comgatible Polymers 6(3): 241-246.
Perera, G., J. Rombach and A Bernkop-Schnurch (2010). "Hydrophobic thiolation of pectin with 4-aminothiophenol: synthesis and in vitro characterization." AAPS PharmSciTech 11(1): 174-180.
Prestwich, G.D., D. M. Marecak, J. F. Marecek, K. P. Vercruysse and M. R. Ziebell (1998). "Controlled chemical modification of hyaluronic acid: synthesis, applications, and biodegradation of hydrazide derivatives." Journal of Controlled Release 53(1): 93-103.
Quinn, M. E. and P. J. Sheskey (2009). Sodium Hyaluronate. Handbook of Pharmaceutical Excigients Sixth Edition. R. C. Rowe, P. J. Sheskey and M. E. Quinn. London Chicago, Pharmaceutical Press: 646-648.
Serban et al., "Synthesis, characterization and chondroprotective properties of a hyaluronan thioethyl ether derivative", Biomaterials, vol. 29, Issue 10, 2008, pp. 1388-1399.

* cited by examiner

THIOL-MODIFIED HYALURONAN AND HYDROGEL COMPRISING THE CROSSLINKED HYALURONAN

The present invention relates to a thiol-modified hyaluronan, a sterile hydrogel composition, comprising a crosslinked polymer, wherein the crosslinked polymer is an oxidation product of the thiol-modified hyaluronan, as well as uses thereof and a method for producing the same.

STATE OF THE ART

Hyaluronan, abbreviated HA, also called hyaluronic acid and its salts, e.g. sodium hyaluronate, is a naturally occurring anionic, non-sulfated glycosaminoglycan with repeating disaccharides being composed of D-glucuronic acid and N-acetyl-D-glucosamine.

High molecular weight hyaluronan is naturally present in the skin and is known for its viscoelastic properties and also for its very high propensity to absorb water. Its properties contribute to a large extent to the elasticity of the skin. Given its properties and its qualities of biocompatibility, tolerance and lack of toxicity, advantage has thus been taken of this compound for more than 10 years now in many applications in the medical and cosmetics fields, in particular aesthetic procedures. For instance, hyaluronan is used for filling wrinkles via direct injection into the dermis in the area under consideration (use as dermal filler).

Highly purified unmodified HA of biofermentative origin is perfectly biocompatible and identical to endogenous hyaluronan. However, despite having the advantage of being highly compatible with the tissues of the human body, having a high affinity for water and performing a strong moisturising function, HA does not have adequate biomechanical properties. When HA is injected into skin tissues, there is a rapid in vivo degradation by both hyaluronidases (enzymatic degradation) and free radicals (chemical degradation) present in the tissues of the human body.

Numerous solutions have been proposed to slow down the in vivo degradation of HA and to modify its chemical, physical, and biological properties, additionally providing increased resistance of the formulations to degradation during storage, to heat and therefore to sterilization.

These approaches typically involve chemical modification of HA including for example crosslinking of HA by chemical, enzymatic or photochemical means. These crosslinked hyaluronan gels can be obtained by various preparation processes. Generally, these processes require two main steps, the first consisting of hydrating hyaluronan in order to convert it into an aqueous solution and the second aimed at crosslinking the HA molecules of said aqueous solution in the presence of an agent capable of inducing the crosslinking thereof (also referred to as "crosslinking agent"). Examples of crosslinking agents include formaldehyde, divinyl sulfone, biscarbodiimides, and epoxides.

For the production of dermal fillers, the crosslinking agent is most commonly chosen from epoxides, such as 1,4-butanediol diglycidyl ether (BDDE) or 1,2,7,8-diepoxyoctane (DEO), aldehydes, or poly vinylsulfones, such as divinylsulfone (DVS), and is therefore synthetic in nature.

Unfortunately, chemical modifications lead to side effects and foreign body reactions not observed with unmodified HA, which has naturally low immunogenicity and no toxicity. In the majority of marketed HA soft tissue fillers BDDE is used as a crosslinking agent. Due to the reactive nature of the epoxide groups present in BDDE, non-reacted BDDE remaining in the dermal filler might have genotoxic effects. Thus, BDDE in dermal fillers has to be maintained at trace amounts (<2 parts per million), so that expensive additional purification and test procedures are needed during production. Although the safety profile of BDDE crosslinked fillers is supported by long term clinical experience (De Boulle, Glogau et al., 2013, A review of the metabolism of 1,4-butanediol diglycidyl ether-crosslinked hyaluronic acid dermal fillers, Dermatol Surg (39): 1758-1766), BDDE may still raise some safety concerns (Choi, Yoo et al., 2015, Modulation of biomechanical properties of hyaluronic acid hydrogels by crosslinking agents, J Biomed Mater Res Part A (103A): 3072-3080).

Due to the genotoxic risks associated with BDDE, the yearly dose of dermal filler products such as Juvederm®, which may be applied over the lifetime of a patient, is limited to 20 mL per year. Administration of the commercially available dermal filler product Restylane® is limited to a volume of 6 mL per application. Similar limitations apply to dermal fillers comprising DVS crosslinked hyaluronan.

Another problem with chemical modifications is the necessity of harsh reaction conditions, such as alkaline pH values and high temperatures (above 50° C.) to which hyaluronan has to be subjected during the crosslinking reaction in order to achieve the desired degree of crosslinking. It is known that the molecular weight of HA decreases because of hydrolytic degradation during exposure to acidic (pH below 4) or alkaline pH (pH above 10). In addition, hyaluronan is degraded at higher temperatures above 40° C. (Troncoso et al., 2016, A kinetic study of the degradation of Hyaluronic acid at high concentrations of sodium hydroxide, student thesis, accessed online via http://uu.diva-portal.org/smash/get/diva2:954372/FULLTEXT01.pdf; Stern et al., 2007. The many ways to cleave hyaluronan, Biotechnology Advances (25): 537-557; Tokita and Okamoto, 1996, Degradation of hyaluronic acid—kinetic study and thermodynamics, Eur. Polym. J. (32): 1011-1014). It is further known that low molecular weight hyaluronan fragments with a molecular weight of less than about 200 kDa have pro-inflammatory effects (Naor, 2016, Editorial: Interaction Between Hyaluronic Acid and Its Receptors (CD44, RHAMM) Regulates the Activity of Inflammation and Cancer, Frontiers in immunology 7:39; Monslow et al., 2015, Hyaluronan—a functional and structural sweet spot in the tissue microenvironment, Frontiers in immunology 6:231).

Disulfide cross-linked hyaluronan hydrogels were first described by Shu et al. (Biomacromolecules 3, 1304-1311, 2002).

The disulfide crosslinked derivative of a thiol-modified hyaluronan (HA-SH) may be obtained by a self-crosslinking mechanism. A network of crosslinked hyaluronan polymers establishes upon formation of disulfide bonds between thiol groups (HA-S-S-HA). The thiol group forming a disulfide bond may connect the pendant groups of a common HA backbone molecule or a neighbouring HA molecule, i.e. the crosslinking may be intramolecular or intermolecular, respectively. The formation of disulfide bonds from free thiol groups is an oxidation reaction that may occur spontaneously, e.g. due to ubiquitous oxygen, or upon addition of an oxidation agent.

WO 2004/037164 further studied hyaluronan modified with 3,3'-dithiobis(propanoic dihydrazide) (DTP) or 4,4'-dithiobis(butyric dihydrazide) (DTB). Gels obtained by disulfide formation and use of thiol reactive agents such as polyethylenglycol di(meth)acrylic acids for crosslinking were evaluated for their potential in tissue engineering, i.e. as a scaffold for growth and culture of cells for implantation.

In WO 2005/056608 the same techniques were employed to crosslink a thiolated hydrazide modified carboxymethyl hyaluronan to obtain macromolecular cell scaffolds. Serban et al. describe the synthesis of a 2-thioethyl ether hyaluronan derivative (Biomaterials 29, 1388-1399; 2008), which however was unsuitable for crosslinking by the investigated crosslinking agents. EP 2 103 631 describes thiol-modified macromolecules including hyaluronic acid, wherein a thiol group is introduced by a hydrazide coupling method, and its cross-linked products. The crosslinked products are either obtained with a crosslinking agent or by disulfide formation.

The synthesis of thiolated hyaluronic acid was also described in Kafedjiiski et al. (Int J Pharm 343, 48-58; 2007) as well as its potential use in drug delivery, wound healing and tissue repair. CN101367884A discloses the synthesis of HA-cysteamine conjugates which comprise both free thiol groups and disulfide groups. EP 2 614 828 describes thiol-modified biocompatible polymer derivatives with a low degree of modification and cross-linked materials thereof. WO 2008/077172 describes thiolated hyaluronic acid for tissue augmentation. In one example, WO 2008/077172 describes an intradermal application of a sterile hydrogel formulation with 2 g thiol-group containing hyaluronic acid (thiol-modified hyaluronan), wherein a depot formed by the thiol-group containing hyaluronic acid could be tactually detectable over two weeks; however, the document is silent about the specific features of the thiol-modified hyaluronan used in this example.

The inventors of the present invention further studied the potential of self-crosslinked thiol-modified hyaluronan hydrogels as soft tissue fillers. For soft tissue fillers is it desired that the implanted hydrogel remains at the site of implantation over an extended time period and thus, achieves a sustainable effect due to slow degradation.

However, initial in vivo studies with hydrogel compositions based on self-crosslinked thiol-modified hyaluronan showed faster degradation behavior after implantation in comparison to dermal fillers with an external crosslinking agent. Moreover, with respect to optimizing the residence time for specific applications, it is desirable to have access to hydrogels with different rheological properties. Accordingly, it is an object of the present invention to provide a thiol-modified hyaluronan (HA-SH) for a composition comprising a disulfide crosslinked polymer, which allows to optimize the composition's properties especially regarding the application as soft tissue filler.

SHORT DESCRIPTION OF THE INVENTION

The present invention provides a thiol-modified hyaluronan, wherein the thiol-modified hyaluronan comprises a plurality of modification groups with a thiol-group in the hyaluronan side-chains and wherein the modification group comprises an amino acid residue with basic side chain and a conjugated terminal naturally occurring amino-thiol, preferably the amino-thiol is selected from the group consisting of cysteamine, cysteine, homocysteine and esters of cysteine or homocysteine.

In another aspect, the present invention provides a sterile hydrogel composition comprising a crosslinked polymer, wherein the crosslinked polymer is an oxidation product of the thiol-modified hyaluronan according to the invention. The sterile hydrogel composition according to the present invention is a hydrogel based on a modified hyaluronan with thiol groups (HA-SH), wherein the hyaluronan is cross-linked by disulfide bonds between the thiol groups of the modified hyaluronan (oxidation product of a thiol-modified hyaluronan). The oxidation product is a copolymer consisting of sections of unmodified hyaluronan and of modified hyaluronan, the latter being connected via disulfide bonds.

The modification group of the thiol-modified hyaluronan comprises or consists of a residue derived from an amino acid with basic side chain, preferably a proteinogenic amino acid, and a naturally occurring amino-thiol, which is conjugated at a terminal position such that the thiol-group remains free. Thus, the thiol-modified hyaluronan and the composition advantageously may be composed of highly biocompatible and non-toxic components, for example, the thiol-modified hyaluronan HA-LYSC, wherein the modification group consists of lysine and cysteamine.

The hydrogel is free of any additional external bifunctional crosslinking agents, such as divinyl sulfone. With the plurality of modification groups having a free thiol-group, the thiol-modified hyaluronan can be crosslinked by oxidation and it was shown that the thiol-modified hyaluronan according to the invention allows for preparing hydrogel compositions comprising the disulfide crosslinked thiol-modified hyaluronan (Examples 7 to 10). Compositions according to the invention were shown to have good in vivo performance in terms of residence time in soft tissue and biocompatibility (Examples 12 and 13).

An amino acid with a basic side chain is a weak base and its side chain may be positively charged. Accordingly, the novel thiol-modified hyaluronan (HA-SH) comprises a basic side chain and thus a positively ionisable feature in addition to a distal thiol group. The inventors found that the thiol-modified hyaluronan according to the invention as well as the hydrogel compositions comprising the disulfide cross-linked thiol-modified hyaluronan have a number of surprising rheological properties.

For example, the inventors found that solutions of thiol-modified hyaluronan comprising a positively charged lysine modification group show a significantly decreased viscosity compared to solutions prepared with thiol-modified hyaluronans comprising neutral or negatively charged modification groups in their side-chains (see Example 14, Table 7). Without wishing to be bound by theory, it is assumed that the observed rheological effect is caused by a distortion of hyaluronan's rigid hydrogen bonding network through the positively charged lysine residues. A lower viscosity of aqueous solutions of thiol-modified hyaluronan comprising a positively charged lysine modification group in turn provides the possibility to access higher concentrated solutions, which result in crosslinked hydrogels with a more natural, lower elastic modulus and acceptable extrusion force.

When comparing the in vivo residence time of hydrogels based on crosslinked thiol-modified hyaluronan with a similar degree of modification, a slower decrease of the mean relative depot volume was found for hydrogels comprising crosslinked thiol-modified hyaluronan in higher concentrations (Example 12, Table 6). However, due to the exceptionally high elastic modulus of compositions comprising conventional thiol-modified hyaluronans, which is exceeds 1000 mPa, there are limits for further increasing the concentration in order to increase the residence time of implants. Consequently, for conventional thiol-modified hyaluronan polymers, the maximum concentration limit in a crosslinked composition seems to be in the range of 20 mg/mL.

Besides concentration of the thiol-modified hyaluronan, a second crucial parameter determining the residence time of a dermal filler can be its elastic modulus G' (Guarise et al., 2019, HA-based dermal filler: downstream process comparison, impurity quantitation by validated HPLC-MS analysis, and in vivo residence time study, Journal of Applied Biomaterials & Functional Materials, 173: 1-9). Highly crosslinked hyaluronic acid fillers, having in turn an unnaturally high elastic modulus, are prone to trigger adverse effects more likely (Keizers et al., 2018, A high crosslinking grade of hyaluronic acid found in a dermal filler causing adverse effects, Journal of Pharmaceutical and Biomedical Analysis, 159: 173-178).

When comparing sterile hydrogel compositions comprising a crosslinked hyaluronan-lysyl-cysteamine polymer with sterile hydrogel compositions comprising a conventional thiol-modified hyaluronan (hyaluronan-cysteamine) in the same concentration, the compositions comprising hyaluronan-lysyl-cysteamine polymer had a significantly lower elastic modulus G' (see Example 11, Table 5). Surprisingly, these compositions showed an in vivo degradation rate which was comparable to the degradation rate observed after implanting compositions comprising crosslinked conventional thiol-modified hyaluronan (see Example 12, Table 6).

When using thiol-modified hyaluronans with a lysine comprising modification group, compositions comprising even higher concentrations of the thiol-modified hyaluronan derivative can be produced, which finally allows the application of an increased amount of crosslinked thiol-modified hyaluronan per implant to further prolong the in vivo residence time.

In one embodiment, the thiol-modified hyaluronan shows a dynamic viscosity of below 300 mPa*s, wherein the dynamic viscosity is determined with a cone-plate system, e.g., using a cone-plate rheometer such as an Anton Paar MCR 102 rheometer, at a temperature of 25° C. and a constant shear rate of 5/s based on an aqueous, preferably acidic, solution of the thiol-modified hyaluronan in a concentration of 1.2% by weight. Preferably the dynamic viscosity determined as defined above is below 250 mPa*s, more preferably below 200 mPa*s.

In a preferred embodiment of the thiol-modified hyaluronan, the modification group is linked to the hyaluronan via a carboxamide, wherein the acyl group of the carboxamide originates from the carboxyl group of the glucuronic acid moiety in the hyaluronan. In other words, the modification group is conjugated to the hyaluronan's carboxyl group to form a carboxamide. Preferably, the carboxamide is formed together with an amino group of the amino acid, which may be either the amino group in alpha-position to its carboxyl group or an amino group in the basic side chain of the amino acid residue.

The modification group comprises a conjugated terminal naturally occurring amino-thiol, i.e. a moiety with an amino group and a (free) thiol group. In a preferred embodiment, the amino-thiol is selected from the group consisting of cysteamine, cysteine, homocysteine and esters of cysteine or homocysteine.

It is preferred that the amino-group of the amino-thiol is conjugated to the amino acid's carboxyl group to form a carboxamide.

Accordingly, in some embodiments, the components of the modification group are linked with amide bonds and the modification group is linked to the hyaluronan by an amide bond. Amide bonds are preferred due to their stable and nevertheless biocompatible nature.

The amino acid residue with basic side chain preferably is derived from an alpha amino acid, e.g. a proteinogenic amino acid, such as lysine, arginine or histidine, most preferably it is derived from lysine.

For example, the modification group comprises an amino acid residue based on lysine and the amino-thiol cysteamine, wherein the amino group of the cysteamine is conjugated to the carboxyl group of the lysine. The respective thiol-modified hyaluronan with this modification group herein is referred to as HA-LYSC. The thiol-modified hyaluronan HA-LYSC has a substructure according to formula (I) or formula (II) or both

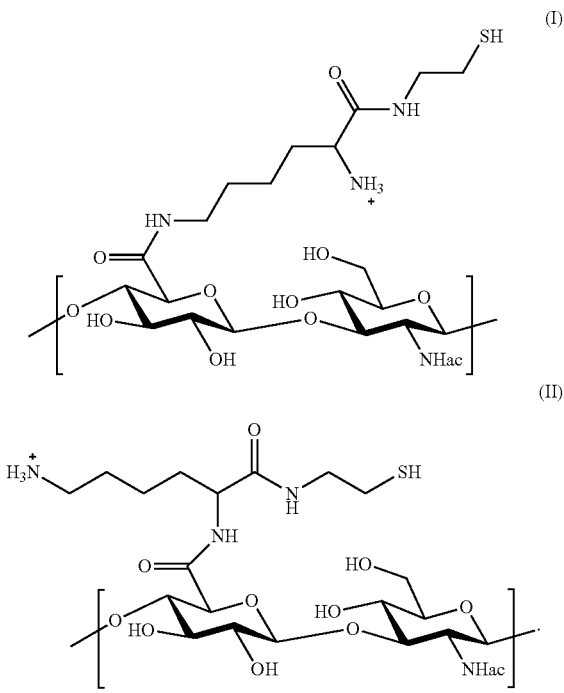

In a preferred embodiment, the thiol-modified hyaluronan has a substructure according to formula (II). An analysis of the binding modality of the lysine in certain thiol-modified hyaluronans investigated herein indicated that the lysine is bound via the amine at the alpha-CH (Example 16).

In another preferred embodiment, the thiol-modified hyaluronan has a degree of modification with thiol groups of more than about 80 µmol per gram polymer, preferably more than about 105 µmol per gram polymer, more preferably more than about 120 µmol per gram polymer, and the thiol-modified hyaluronan has a degree of modification with thiol groups of less than about 320 µmol per gram polymer, preferably less than about 290 µmol per gram polymer, more preferably less than 250 µmol per gram polymer.

The inventors further found that the degree of modification of hyaluronan with thiol groups is another important feature for influencing the in vivo residence time of the sterile hydrogel.

The "degree of modification with thiol groups", indicates the initial amount of thiol groups (typically given in µmol) per gram (g) of the thiol-modified hyaluronan and may be abbreviated as DoM. This amount of thiol groups is a characteristic of the thiol-modified hyaluronan raw material and indicates the amount of thiol groups, which are available for crosslinking during the production process of the composition. Thiol groups or moieties may also be referred to as mercapto or sulfhydryl groups. Based on various examples with hyaluronan-cysteamine, the inventors identified an optimal range for the degree of modification between about 80 µmol per g polymer to about 320 mol per g polymer. On the one hand, a degree of modification above 80 mol per g polymer was necessary to produce compositions with a volumizing effect of more than 12 weeks after implantation. On the other hand, using thiol-modified hyaluronan with higher degrees of modification did not result in a volumizing effect of the produced hydrogel, i.e. an increase in the depot volume (e.g. >335 mol per g polymer, data not shown).

Besides the degree of modification, parameters that remarkably influence the rheological and in vivo properties of the hydrogel are the molecular weight distribution of the hyaluronan chains, the degree of crosslinking and the concentration of the crosslinked thiol-modified hyaluronan.

Preferably, the thiol-modified hyaluronan has a mean molecular weight (MMW) of at least about 400 kDa, preferably at least about 500 kDa, more preferably at least about 600 kDa, such as about 700 kDa.

On the other hand, the thiol-modified hyaluronan preferably has a mean molecular weight (MMW) of at most about 4,500 kDa, in particular at most a mean molecular weight in the range of from 4,000 kDa to 4,200 kDa. It was found that hyaluronan starting materials with even higher molecular weight specification are not available in quantity and quality necessary for preparing a thiol-modified hyaluronan suitable for preparing sterile hydrogel compositions in industrial scale and/or as dermal filler. More preferably, the thiol-modified hyaluronan has a mean molecular weight of at most 3,500 kDa or at most 2,000 kDa. For example, the mean molecular weight of the thiol-modified hyaluronan may be in the range of from about 700 kDa to about 2,000 kDa.

A high degree of crosslinking (via oxidation of the thiol groups) is beneficial for obtaining hydrogel compositions with elastic properties suitable for a volumizing soft tissue filler. In order to provide hydrogel compositions with reproducible and stable characteristics such as the rheological properties, the crosslinking of the thiol-modified hyaluronan (i.e. the formation of disulfide bonds) should be mostly complete before the hydrogel is further processed (i.e., undergoing further processing steps such as sieving, homogenization, filling into syringes and sterilization). However, a certain small amount of thiol groups might not be available for disulfide formation due to factors like sterical hindrance.

The sterile hydrogel composition according to the invention has a residual thiol content of less than 20% in respect to the degree of modification of the thiol-modified hyaluronan. This corresponds to more than 80% of the available thiol groups of the thiol-modified hyaluronan being oxidized during the hydrogel production process. The fraction of non-crosslinked thiol groups in the crosslinked polymer may be determined via the residual thiol content expressed in μmol per g polymer. High and uniform oxidation rates and thus a reproducible low residual thiol content in the sterile hydrogel composition are obtainable by use of an oxidation agent, e.g. hydrogen peroxide, during oxidizing step in the production method.

Within the hydrogel composition according to the invention, it is preferred that the residual thiol content is less than 15% in respect to the degree of modification of the thiol-modified hyaluronan.

Preferred concentrations were identified to be from about 4 mg/mL to about 50 mg/mL. On one hand, the thiol-modified hyaluronan may comprised in the composition with a concentration of at most 50 mg/mL, preferably at most 35 mg/mL, more preferably at most 25 mg/ml, in particular at most 18 mg/mL. On the other hand, the thiol-modified hyaluronan may be comprised in the composition with a concentration of at least 4 mg/ml, more preferably at least 5 mg/mL, more preferably at least 7 mg/ml.

Preferably, the hydrogel composition comprises the oxidation product of the thiol-modified hyaluronan in a concentration of from about 7 mg/mL to about 35 mg/mL, more preferably of from about 13 mg/mL to about 25 mg/mL, e.g. 18 mg/mL or 22 mg/mL.

The concentration of the thiol-modified hyaluronan in mg/mL is given by weight in respect to the volume of the sterile hydrogel composition. The concentration preferably refers to the concentration of the salt, e.g. the sodium salt of the crosslinked thiol-modified hyaluronan. Accordingly, an equivalent amount of thiol-modified hyaluronan is provided for the preparation. Higher concentrations are not considered suitable as they result in hydrogel compositions with high viscosities without acceptable injectability. However, due to the low viscosity of the thiol-modified hyaluronan according to the invention, higher concentrations are possible such that the composition could comprise up to 50 mg/mL thiol-modified hyaluronan. It was found that hydrogels comprising the thiol-modified hyaluronan in a concentration of up to 35 mg/mL showed an extrusion force acceptable for dermal injection. Concentrations of 4 mg/mL or lower are not considered suitable due to low elastic modulus G' observed for such hydrogel compositions, resulting in faster in vivo degradation. Within the range of about 5 mg/mL to about 25 mg/mL, e.g. 7 or 18 mg/mL, good rheological properties were observed.

In another aspect, the invention provides the composition according to the invention for use as medicine, in particular for use in the treatment and prevention of soft tissue conditions. Furthermore, the invention relates to the cosmetic use of the composition according to the invention. Such uses (therapeutic or cosmetic) may be referred to the use of the composition according to the invention as soft tissue filler or for tissue augmentation. Such uses preferably include the application, e.g. by injection or implantation, to a human being, while the applicability is not limited to the human species.

In another aspect, the invention relates to a method, wherein the method comprises introducing the composition according to the invention, e.g. by injection from a syringe, at a specific soft tissue site. The method relates to the use of the composition as soft tissue filler or for tissue augmentation for therapeutic as well as cosmetic purposes.

In one embodiment, uses or methods according to these aspects comprise that the hydrogel composition is introduced into a tissue site by injection from a syringe intradermally, supraperiosteally or subcutaneously into a human being.

DETAILED DESCRIPTION OF THE INVENTION

The "thiol-modified hyaluronan" (HA-SH) is a thiol-group containing derivative of a hyaluronic acid (HA). According to the present invention, the thiol-modified hyaluronan comprises a plurality of modification groups including a basic group linked to hyaluronan. It is accessible via known synthetic approaches starting off from hyaluronan which is available in different molecular weights (or molecular weight ranges). Numerous examples of HA modification with thiol group containing modifications groups can be found in scientific and patent literature:

Griesser et al. provides a review of thiolated hyaluronic acid polymers (Griesser et al., Polymers 10 (2018) 243). Aeschlimann (EP 1 115 433 B1) describes a method of functionalization of HA which does not compromise the molecular weight of HA and which further provides HA molecules that are well tolerated in vivo and are biodegradable. The method is used to generate HA with different terminal functional groups for crosslinking, such as thiol groups. These side chains are introduced into HA by carbodiimide-mediated coupling of primary (protected) thiol group containing amines or disulfide-bond containing diamino or dihydrazide ligands to the carboxyl group of the glucuronic acid moiety using an active ester intermediate. Intermediate products with disulfide bonds are then reduced and intermediate products with protected thiol groups are then deprotected by removing the protecting group. Another method is described by Bulpitt et al. (U.S. Pat. No. 6,884,788) which comprises a direct reaction of the HA carboxyl group with a disulfide-bond containing carbodiimide (such as 2,2'-dithiobis(N-ethyl-(N'-ethylcarbodiimide), followed by reducing the disulfide bond with a reducing agent. WO 2008/008857 A2 discloses synthesis methods for 2-thioethyl ether derived hyaluronan. EP 0 587 715 discloses how to synthesize water insoluble anionic polysaccharides via dissolving at least one polyanionic polysaccharide (e.g., HA), in an aqueous mixture; activating the polyanionic polysaccharide with an activating agent such as a diimide, e.g. EDC or ETC, or BOP; modifying the activated polyanionic polysaccharide with a modifying compound such as 1-hydroxybenzotriazole hydrate (HOBt) or 1-hydroxy-benzotriazole monohydrate; and reacting the activated polyanionic polysaccharide with a suitable nucleophile (such as an amino thiol) to form the desired insoluble composition. The inventors state that one major advantage of the BOP activation of polyanionic polysaccharide is that the molecular weight of the polyanionic polysaccharide is not decreased upon coupling to the nucleophile. EP 1 790 665 B1 describes a water-soluble modified hyaluronic acid, which is produced by introducing a substituent into the carboxy group of the glucuronic acid of hyaluronic acid, via an amide bond using a BOP condensing agent in an aprotic polar solvent. Diamines with a disulfide bond are among the listed substituents. Triazine-mediated amidation with DMT-MM for efficient and controlled functionalization of hyaluronic acid with cysteamine is described in Borke et al., wherein the mild reaction conditions and the minimal degradation of the polysaccharide chain are listed as advantages of using this group of coupling agents in comparison to other coupling reagents such as EDC-mediated substitution (Borke et al., Carbohydrate Polymers 116 (2015) 42-50). Liang et al. describe the introduction of thiol groups to HA via an amidation reaction of the side carboxylates with cystamine in the presence of CDMT and NMM, followed by a reducing reaction with DTT (Liang et al. Carbohydrate Polymers 132 (2015) 472-480). The thiol modification of HA with 1-cysteine ethyl ester hydrochloride by means of the double catalytic system—carbodiimide/Nhydroxysuccinimide was described in Kafedjiiski et al. (Int J Pharm 343, 48-58; 2007). In WO 2004/037164 hyaluronan was modified with 3,3'-dithiobis(propanoic dihydrazide) (DTP) or 4,4'-dithiobis(butyric dihydrazide) (DTB). After reduction with a reducing agent such as DTT the corresponding thiolated HA derivatives HA-DTPH and HA-DTBH were obtained. EP 2 103 631 also describes introduction of a thiol group bearing ligand via the carboxylic groups of HA by a hydrazide coupling method. Different thiolated HA polymers (HA-DGDTPDH, HA-DPDTPDH, HA-DSCDH) were synthesized.

During preparation of the thiol-modified hyaluronan according to the invention, the modification group is introduced by a modification agent. In a preferred embodiment, the modification agent reacts with the carboxyl group of the glucuronic acid moiety in the hyaluronan, such that the modification group is linked to the hyaluronan via a carboxamide bond. Accordingly, the modification agent for synthesis of the thiol-modified hyaluronan according to the invention preferably comprises at least one amino group capable to form the amide bond with the carboxyl group of the glucuronic acid moiety in the hyaluronan and the modification agent comprises a thiol group.

Preferably, modification agents are derivatives of the amino-thiols, e.g. cysteamine, cysteine, homocysteine or esters of cysteine or homocysteine, wherein the N-terminus (amino-group) is coupled with the carboxyl group of the amino acid, e.g. the amino acid lysine. These modification agents are preferably synthesized by amidation of N-protected lysine with cysteamine, cysteine, homocysteine or esters of cysteine or homocysteine, using routine peptide coupling reagents, preferably those enabling facile product purification, e.g. through removal of reactants and side products by an aqueous extraction upon reaction work up (see Example 15). Alternatively, cysteamine, cysteine, homocysteine or esters of cysteine or homocysteine are reacted with corresponding active esters of N-protected lysine in organic solvents, such as succinimidyl esters. In a preferred embodiment, the thiol-modified hyaluronan is a hyaluronan-lysyl-cysteamine, wherein the lysine moiety is linked to hyaluronan via an amide bond. Thus, the appropriate modification agent may be N-protected bis(Lysyl)-cystamine.

Regioselectivity of the coupling reaction linking the amino acid with the hyaluronan via amide bond formation can be controlled, for example, by appropriate N-protection of the modification agent. A regioselective coupling to hyaluronan was achieved using unprotected bis(lysyl)-cystamine (Example 15 A) as discussed in Example 16. Apparently, reaction conditions during amide coupling, e.g. pH control in the aqueous system, ensure the regioselectivity of the reaction. In Example 15 B, the preparation of bis (epsilon-azido-L-lysyl)-cystamine dihydrodchloride is described, which modification agent has an azide protecting group masking the epsilon-amino group, such that only the free alpha-amino group is reactive under amidation conditions. Subsequently, the masked amino group can be deprotected in parallel to disulfide reduction by application of excess amounts of reduction agent. Alternatively, regioselective coupling via the epsilon-amino group is achievable by synthesis of bis(alpha-azido-L-lysyl)-cystamine dihydrochloride, which can be prepared by acylation of cystamine with commercially available N-epsilon-t-Butyloxycarbonyl-alpha-azido-L-lysine in analogy to the described protocol.

The properties of the thiol-modified hyaluronan and also of the hydrogel composition according to the invention are critically influenced by the "degree of modification" of the thiol-modified hyaluronan. Established methods for determining the degree of modification include the Ellman method or measuring the release of a chromophoric thione upon reaction of 2,2'-dithiodipyridine with thiol-bearing agent (see Example 1). Those skilled in the art will also know alternative methods resulting in similar values. Herein, the degree of modification is given in μmol of thiol groups per gram polymer. Alternatively, the degree of modification may be indicated as percentage, wherein the amount of modified repeating units is divided by the total amount of HA-repeating units in the polymer (D-glucuronic acid and N-acetyl-D-glucosamine). The degree of modification in μmol of thiol groups per gram polymer can be converted in percentage by taking into account the molecular weight of 400 g/mol of the HA-repeating unit. In this conversion, the change of molecular weight introduced by the modification is typically neglected.

The term "sterile" as used herein is to be understood in accordance with the art specifying a composition complying with the microbiological standards as defined for cosmetic or pharmaceutical products, for example in the United States Pharmacopoeia (USP), the European Pharmacopoeia (Ph. Eur.) or other national standards. Classically, the hyaluronan gels are sterilized after being filled into syringes. Thermal moist-heat sterilization with an autoclave is one of the standard methods, which comprises subjecting the HA gels to high-pressure saturated steam at 121° C. for around 15-20 minutes. Autoclaving for shorter time periods (for example, between about 1 minute and 5 minutes) and at higher temperatures (for example, between about 130° C. and 135° C.) might lead to a better preservation of the molecular weight of the HA molecules in the gels (see M. L. Bernuzzi, A. Giori, "An innovative way to thermally sterilize hyaluronic acid pre-filled syringes", 2016 white paper available under https://www.fedegari.com/wp-content/uploads/2019/03/WP-Fedegari-Thermal-sterilization-PFS-with-Hyaluronic-Acidv-2.pdf, US 2016/0220729). The optimization of other autoclaving parameters (such as ensuring rapid cooling of the product) might be additionally advantageous for preserving the molecular weight of the polymer (http://www.steriflow.com/en/news/Sterilization-hyaluronic-acid).

The term "hydrogel" as used herein is to be understood as describing a composition, which has both solid and fluid (liquid) characteristics. On one hand, the hydrogel may be injectable, i.e. it shows a fluid-like behavior. On the other hand, the hydrogel may be stiff (or rigid) enough to maintain a certain form, e.g. the hydrogel may be provided in the form of a preformed implant, thread or a filament. Thus, the term hydrogel alone does not limiting the rheological properties of the composition in a quantitative manner.

The invention also provides a method for producing a hydrogel composition according to the invention comprising the steps of:
a) providing a thiol-modified hyaluronan, wherein
  the thiol-modified hyaluronan comprises a plurality of modification groups with a thiol-group in the hyaluronan side-chains, wherein the modification group comprises an amino acid residue with basic side chain and a conjugated terminal naturally occurring amino-thiol,
  in an aqueous solution,
b) oxidizing the thiol-modified hyaluronan by exposing the previously obtained aqueous solution to conditions that allow the thiol-modified hyaluronan to form a disulfide crosslinked polymer, wherein or whereby the aqueous solution becomes a hydrogel, wherein said hydrogel has a residual thiol content of less than 20% in respect to the degree of modification of the thiol-modified hyaluronan,
optionally c) adding an unmodified polymer selected from the group of biocompatible polysaccharides to the previously obtained hydrogel or to the previously obtained solution,
optionally d) sieving the previously obtained hydrogel to obtain a hydrogel with a particular particle size distribution,
e) filling the previously obtained hydrogel into a container, preferably a syringe, and exposing the filled container to conditions allowing for sterilization of the hydrogel,
f) obtaining a sterile hydrogel composition in a container comprising a crosslinked polymer.

In the method for producing a hydrogel the steps may be conducted in different sequences. Especially the steps of crosslinking (oxidizing), adding an unmodified polymer and sieving may be performed in different sequences without necessarily affecting the hydrogel quality. Preferably, the steps are conducted in the sequence a), c), b), d), e) and f), wherein the preparation of the solution (step a) and the addition of the unmodified polymer (step c) may be performed concomitantly and optionally a further component (e.g. a local anaesthetic agent) may be added at the same time.

Formation of disulfide bonds (crosslinking) naturally occurs at physiological pH values in the presence of oxygen (e.g. supplied via the surrounding air or dissolved in an aqueous solution). However, addition of an oxidation agent is preferred to ensure that the conditions in step b) are sufficient to reach the degree of oxidizing which ensures that the hydrogel has a residual thiol content of less than 20% in respect to the degree of modification of the thiol-modified hyaluronan. The active addition of an oxidizing agent accelerates and completes disulfide formation to obtain the desired low degree of residual thiol content. Moreover, adding an oxidation agent in step b) turned out to be especially relevant to ensure a reproducible and uniform result in industrial processes, i.e. including large bulk volumes.

Accordingly, in a preferred embodiment, in step b) an oxidation agent is added to the previously obtained aqueous solution.

Suitable and well established oxidizing agents are for example hydrogen peroxide (or other peroxides), dehydroascorbic acid, dimethyl sulfoxide and hypochlorous acid (sodium hypochlorite). Under excess pressure conditions pure oxygen gas or a high oxygen gas mixture can be used to increase the concentration of oxygen available as oxidation agent in the polymer aqueous solution. The preferred amount to be added depends on the oxidation agent and the amount of thiol groups in the thiol-modified hyaluronan. Exemplarily, for hydrogen peroxide, in step b) the molar ratio of free thiol groups of thiol-modified hyaluronan to hydrogen peroxide should be preferably at most 4:1; more preferably at most 2:1.

In the context of hydrogels, the elastic modulus G' of the hydrogel composition is typically used to characterise its elastic properties and denotes the shear storage modulus as determined with a rheometer applying shear force e.g. by rotating a (cone-)plate. Standard methods for determining the elastic modulus G' are known in the art (Stocks D., Sundaram H., Michaels J., Durrani M. J., Wortzman M. S., Nelson D. B., Rheological Evaluation of the Physical Properties of Hyaluronic Acid Dermal Fillers, 2011, *Journal of Drugs in Dermatology*, 10(9), 974-980). The elastic modulus G' is used to characterize the firmness (hardness) or softness of a gel. At the same time it is a measure for the gel's ability to resist deformation. In consequence, dermal filler hydrogels with high G' values are expected to provide better support and volumization after implantation (Stocks et al., 2011). Besides temperature and frequency of the rotating plate other variable testing conditions can influence the quantitative comparability of the elastic modulus G'. Repeated testing may typically result in a standard variation of about ±10% to the mean value e.g. 8%. In some cases it was observed that the elastic modulus varied up to 20% when the hydrogel was provided by extrusion through a needle or without needle. Thus, it is recommended stay close to the protocol as outlined below in Example 4 for assessing the elastic modulus G'.

In a preferred embodiment, the composition further comprises an unmodified polymer selected from the group of biocompatible polysaccharides. Preferably, the unmodified polysaccharide is unmodified hyaluronan (HA). The unmodified (non-crosslinked) or also referred to as free hyaluronan can complement the hydrogel composition. Unmodified HA is commonly added as a lubricant to soft tissue fillers to ensure good injectability by decreasing the extrusion force required to inject the products through a needle or cannula. Preferably, the free hyaluronan raw material used for the production of the composition has a molecular weight in the range of about 500 kDa to about 3,500 kDa. However, due to the fast degradation of unstabilized hyaluronan, the person skilled in the art will understand that the in vivo performance of the composition as soft tissue filler is largely driven by the crosslinked polymer and the properties of the underlying thiol-modified hyaluronan. It is preferred that the unmodified polysaccharide is comprised in a concentration lower than the crosslinked polymer. Exemplarily, an unmodified hyaluronan is comprised in the compositions at concentrations of 3 mg/mL to 7 mg/mL, such as 5 mg/mL, wherein the concentration preferably refers to the concentration of a salt, e.g. sodium hyaluronate.

The hydrogel composition may include a local anaesthetic agent and/or one or more components selected from a variety of other components, such as, growth factors, vitamins, polyalcohols, alkali metal halides, minerals, antioxidants, amino acids, coenzymes, ceramic particles (such as calcium hydroxyl apatite particles), polymeric particles, polymers (such as polyethylene glycol, glycosaminoglycans, lubricins, polysaccharides, and their derivatives), proteins (such as elastin, collagen, keratin, silk fibroin), anti-cellulite agents, anti-scarring agents, anti-inflammatory agents, anti-irritant agents, vasoconstrictors, anti-hemorrhagic agents (such as hemostatic agents and anti-fibrinolytic agents), tensioning agents, anti-acne agents, pigmentation agents, anti-pigmentation agents, anti-phlogistic agents, anti-rheumatic agents, anti-viral agents, anti-infective agents, anti-septic agents, chemotherapeutic agents, cytostatic agents, anti-allergic agents, anti-varicosic agents, analgesics, antibiotics, antimycotics, spasmolytics, antihistamines, agents for treating hemorrhoids, therapeutic agents for treating the skin, and moisturizing agents.

The addition of a local anaesthetic agent to the hydrogel composition is particularly desirable in view of its ability to mitigate pain upon injection. Preferably, the anaesthetic agent is lidocaine, such as in the form of an acid addition salt, e.g. lidocaine HCl.

In a method for producing the hydrogel a local anaesthetic agent and/or one or more components may be added during different production steps, i.e. in one embodiment the local anesthetic agent and/or one or more components is/are added during optional step c) or in another embodiment independently from adding the unmodified polymer e.g. added to the solution during step a) or to the hydrogel obtained in step c) or d). In a preferred embodiment an anaesthetic agent, e.g. lidocaine HCl, is added during step a) or during step c). In an embodiment, wherein step c) precedes step b), i.e. wherein an unmodified hyaluronan is added prior to crosslinking, it is preferred that also a local anaesthetic agent and/or one or more further components are included prior to the crosslinking step.

Furthermore, it will be understood that a main component of the hydrogel composition is water. Preferably water for injection or purified water is used for producing the composition. Besides, it will be acknowledged that the composition may be buffered to exhibit a physiologically acceptable pH in the range of 6.7 to 7.8. Suitable buffers are known to those skilled in the art and include for example phosphate buffer. The composition also exhibits a physiologically-acceptable osmolality, which is similar to the normal osmolality of extracellular fluid in the subject to be treated (e.g. in humans). Thus, the composition may have an osmolality in the range of 250-350 mOsmol/kg and may include additional solutes to adjust the osmolality, such as sodium chloride, calcium chloride, and/or potassium chloride.

The hydrogel composition is sterile and may be used (in a method), wherein the hydrogel composition is a medicine, a cosmetic or medical device. The hydrogel is implanted, preferably by injection through a needle or cannula, at a site of application, preferably a soft tissue. Alternatively, the hydrogel may be implanted via a surgical procedure. Once applied the hydrogel may be referred to as (hydrogel) implant or depot. The hydrogel composition according to the invention is biocompatible and forms an absorbable (i.e. biodegradable) implant. Thus, the hydrogel composition according to the invention is usable as soft tissue filler. The characteristic hydrogel composition according to the invention did show good tolerability and an in vivo volumizing effect after implantation to a soft tissue in rats. These studies support that the hydrogel is a valuable soft tissue filler for various applications.

Soft tissue fillers comprising biomaterials such as stabilized hyaluronan are delivered to the tissue site, where augmentation is desired by means of an injectable hydrogel composition. The aims of the uses or methods referring to soft tissue filling include to augment soft (dermal) tissue, to correct congenital anomalies, acquired defects or cosmetic defects.

The main effect of the hydrogel composition is purely physical as it has a filling effect based on the original volume and the swelling of the implant. Thus, in absence of any physiological or pharmacological interaction, the use may be classified as cosmetic and the composition may be considered as a cosmetic or medical device. Applications, wherein the use of the hydrogel composition according to the invention may be considered as cosmetic include for example the reduction of signs of age, e.g.

application into the tissue of the vulva and vagina for nonsurgical female genital rejuvenation purposes application into the dermis, subdermal or supraperiosteal application.

Exemplarily, the hydrogel composition may be used (in a method) for cosmetic purposes, e.g. for filling wrinkles, for treating skin defects, for restoring lost volume of the face or the body (e.g. breast, ear lobe), for reducing dimples in cellulitis, for treating tear trough deformities, for shaping the contours of the face or the body (e.g. buttock enhancement, hip augmentation, calf augmentation), for penis enlargement (penile girth enhancement, glans penis augmentation).

In other cases the filling and augmentation of a soft tissue may result in a treatment or prevention of a disease, i.e. wherein symptoms of the disease are reduced, alleviated and/or prevented from (re-)occurrence. Disease that are caused by a soft tissue defect may benefit from the temporary and/or local structural filling, damping, support or augmentation of the surrounding tissue by the applied hydrogel. Diseases, wherein the hydrogel composition may be used for treatment or prevention include for example metatarsalgia, a pain disease of the fatty pad of the ball of the foot, for which use the hydrogel composition according to the invention may be applied at the fatty pad of the ball of the foot soft tissue, urinary or fecal incontinence, for which indications the hydrogel composition according to the invention may be applied at the tissue defining sphincters, vulvovaginal atrophy (also genito-urinary syndrome of menopause), for which indication the hydrogel composition according to the invention may be applied at the vulvovaginal area via injection into the vaginal mucosa and the vestibule and/or for labia majora augmentation, wherein a reconstruction of the labia majora will ensure a close contact between both labia majora to protect the inner structures of the vulva vocal cord impairment, venous valve insufficiency, or facial lipoatrophy, debilitating scars or morphological asymmetry or deformation (congenital or resulting as consequence of trauma or surgery, e.g. of the thorax or of the face), for which indications the hydrogel is applied for reconstructive purposes.

In another aspect, the present invention provides an application unit for injection comprising a syringe, wherein the syringe is filled with a hydrogel composition according to the invention and further comprising at least one hypodermic needle. In a preferred embodiment, the unit comprises at least two hypodermic needles, which differ from each other in their lumen. In another embodiment of the application unit, the at least one hypodermic needle is characterized by a lumen measured in Gauge (G) of at least 27 G, preferably of 27 G to 32 G.

Such an application unit is of practical advantage for using and applying the composition according to the invention, be this either for cosmetic or medical purposes.

EXAMPLES

Example 1—Determination of Degree of Modification

Quantification of thiol groups in a thiol-modified hyaluronan (HA-SH) used as raw material for preparation of hydrogel compositions is based on a wet chemistry method employing 2,2'-dithiodipyridine (DTDP). Free thiol moieties which are covalently bound to a polymeric backbone undergo thiol-disulfide exchange reaction with DTDP, whereas one equivalent of a chromophoric thione is released. In buffered acidic medium (pH=4), the absorption of the resulting thione can be measured photometrically at 343 nm.

About 420 mg of thiol-modified hyaluronan were accurately weighed and dissolved in 30 g of 0.01 N HCl under continuous magnetic stirring for 2-3 hours to prepare a stock solution. Then, about 310 mg of the stock solution were accurately weighed and mixed with 4200 mg acetate buffer pH 4 in an eppendorf tube to prepare a sample solution. Three sample solutions were prepared from each stock solution. 25.0 mg N-acetylcysteine were accurately weighed and solved in 25.0 mL of acetate buffer (pH 4). This solution was then further diluted with acetate buffer (pH 4) for the preparation of a calibration curve. Acetate puffer was used for the blank value. 500 μL of a solution containing 0.125 mg/mL of DTDP in acetate buffer (pH 4) were added to 500 μL of each sample of each solution (calibration curve, sample solution and blank value). The solutions were briefly homogenized and incubated for 30 min at room temperature. Finally, each sample (calibration curve, sample solution and blank value) was transferred into a microcuvettes and measured at 342 nm in a spectrophotometer against the blank value.

Example 2—Determination of Residual Thiol Content

For the determination of the residual thiol content of the crosslinked polymer in the hydrogel composition (i.e. the HA-SH polymer after crosslinking and production of the compositions) a similar method as described above was used.

About 50 mg of each sample gel were accurately weighed and mixed with 1.3 mL of a solution containing 0.125 mg/mL of DTDP in acetate buffer (pH 4). 25.0 mg N-acetylcysteine were accurately weighed and solved in 200.0 mL of acetate buffer (pH 4). This solution was then further diluted with acetate buffer (pH 4) for the preparation of a calibration curve. Acetate puffer was used for the blank value. 500 μL of a solution containing 0.125 mg/mL of DTDP in acetate buffer (pH 4) were added to 500 μL of each sample of the calibration curve and the blank. All samples were incubated under continuous agitation for 120 min at room temperature. After centrifugation of all samples 500 μL of each supernatant were further diluted with 500 μL acetate buffer and measured at 342 nm in a spectrophotometer against the blank value.

Example 3—Methods of Producing a Hydrogel

Method A

Dissolution: thiol-modified hyaluronan, unmodified hyaluronan, and lidocaine HCl are concomitantly dissolved in an aqueous solution Crosslinking: After adjustment of the pH to about 6.8 to 7.6 thiol-modified hyaluronan is crosslinked via the oxidation of thiol groups to disulfide bridges by oxygen Sieving: Optionally the hydrogel comprising crosslinked thiol-modified hyaluronan, unmodified hyaluronan and lidocaine HCl is pressed through a filter plate with a defined mesh size (once or multiple times)

Sterilization: Autoclavation after filling of the hydrogel into syringes

Method B

Dissolution: Thiol-modified hyaluronan, unmodified hyaluronan, and lidocaine HCl are concomitantly dissolved in an acidic aqueous solution.

Crosslinking: After adjustment of the pH to about 6.8 to 7.6 thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes

Method C

Dissolution: Thiol-modified hyaluronan is dissolved in an aqueous solution; a separate solution comprising unmodified hyaluronan and lidocaine HCl in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by oxygen.

Sieving: The hydrogel comprising crosslinked thiol-modified hyaluronan is pressed through a filter plate with a defined mesh size (once or multiple times).

Homogenization: The hydrogel comprising crosslinked thiol-modified hyaluronan and the solution comprising unmodified hyaluronan and lidocaine HCl are homogenized and optionally pressed through a filter plate with a defined mesh size (once or multiple times).

Sterilization: Autoclavation after filling of the hydrogel into syringes

Method D

Dissolution: Thiol-modified hyaluronan is dissolved in an aqueous solution; a separate solution comprising unmodified hyaluronan and) lidocaine HCl in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by an oxidation agent and oxygen.

Sieving: The hydrogel comprising crosslinked thiol-modified hyaluronan is pressed through a filter plate with a defined mesh size (once or multiple times).

Homogenization: The hydrogel comprising crosslinked thiol-modified hyaluronan and the solution comprising unmodified hyaluronan and lidocaine HCl are homogenized and optionally pressed through a filter plate with a defined mesh size (once or multiple times).

Sterilization: Autoclavation after filling of the hydrogel into syringes

Method E

Dissolution: Thiol-modified hyaluronan and lidocaine HCl are dissolved in an aqueous solution; a separate solution comprising unmodified hyaluronan in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by oxygen.

Sieving: The hydrogel comprising crosslinked thiol-modified hyaluronan and lidocaine HCl is pressed through a filter plate with a defined mesh size (once or multiple times).

Homogenization: The hydrogel comprising crosslinked thiol-modified hyaluronan and lidocaine HCl and the solution comprising unmodified hyaluronan are homogenized and optionally pressed through a filter plate with a defined mesh size (once or multiple times).

Sterilization: Autoclavation after filling of the hydrogel into syringes.

Method F

Dissolution: Thiol-modified hyaluronan and lidocaine HCl are dissolved in an acidic aqueous solution; a separate solution comprising unmodified hyaluronan in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by an oxidation agent and oxygen.

Sieving: The hydrogel comprising crosslinked thiol-modified hyaluronan and lidocaine HCl is pressed through a filter plate with a defined mesh size (once or multiple times).

Homogenization: The hydrogel comprising crosslinked thiol-modified hyaluronan and lidocaine HCl and the solution comprising unmodified hyaluronan are homogenized and optionally pressed through a filter plate with a defined mesh size (once or multiple times).

Sterilization: Autoclavation after filling of the hydrogel into syringes.

Method G

Dissolution: Thiol-modified hyaluronan, unmodified hyaluronan, and lidocaine HCl are consecutively dissolved in an aqueous solution.

Crosslinking: After adjustment of the pH to about 6.8 to 7.6 thiol-modified hyaluronan is crosslinked via the oxidation of thiol groups to disulfide bridges by oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method H

Dissolution: Thiol-modified hyaluronan, unmodified hyaluronan, and lidocaine HCl are consecutively dissolved in an acidic aqueous solution.

Crosslinking: After adjustment of the pH to about 6.8 to 7.6 thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method I

Dissolution solution 1: Thiol-modified hyaluronan, unmodified hyaluronan and lidocaine HCl are concomitantly dissolved in water.

Crosslinking solution 1: After adjustment of the pH to about 6.8 to 7.6 thiol-modified hyaluronan is crosslinked via the oxidation of thiol groups to disulfide bridges by an oxidation agent and oxygen.

Dissolution solution 2: Thiol-modified hyaluronan, unmodified hyaluronan and optionally lidocaine HCl are concomitantly dissolved in water.

Crosslinking: The pH of solution 2 is adjusted to about 6.8 to 7.6, immediately followed by mixing equal parts of the crosslinked solution 1 with solution 2. Thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method J

Dissolution: Thiol-modified hyaluronan and unmodified hyaluronan are dissolved in an aqueous solution; a separate solution comprising lidocaine HCl is prepared.

Crosslinking: After adjustment of the pH to about 6.7 to 7.8 thiol-modified hyaluronan is crosslinked via the oxidation of thiol groups to disulfide bridges by oxygen.

Sieving: The hydrogel comprising crosslinked thiol-modified hyaluronan and unmodified hyaluronan is pressed through a filter plate with a defined mesh size (once or multiple times).

Homogenization: The hydrogel comprising crosslinked thiol-modified hyaluronan and unmodified hyaluronan and the solution comprising lidocaine HCl are homogenized and optionally pressed through a filter plate with a defined mesh size (once or multiple times).

Sterilization: Autoclavation after filling of the hydrogel into syringes.

Method K

Dissolution: Thiol-modified hyaluronan and unmodified hyaluronan are dissolved in an aqueous solution; a separate solution comprising lidocaine HCl is prepared.

Crosslinking: After adjustment of the pH to about 6.7 to 7.8 thiol-modified hyaluronan is crosslinked via the oxidation of thiol groups to disulfide bridges by an oxidation agent and oxygen.

Sieving: The hydrogel comprising crosslinked thiol-modified hyaluronan and unmodified hyaluronan is pressed through a filter plate with a defined mesh size (once or multiple times).

Homogenization: The hydrogel comprising crosslinked thiol-modified hyaluronan and unmodified hyaluronan and the solution comprising lidocaine HCl are homogenized and optionally pressed through a filter plate with a defined mesh size (once or multiple times).

Sterilization: Autoclavation after filling of the hydrogel into syringes.

Example 4—Determination of Elastic Modulus G'

Oscillatory rheological measurements of all compositions were performed using an Anton Paar MCR 102 Rheometer with a cone-plate system. The compositions were transferred to the rheometer via injection through a 27G needle (or without needle, where indicated). The elastic modulus was obtained during a frequency test with constant deformation within the linear viscoelastic region of the hydrogel at a temperature of 25° C. and a frequency of 1 Hz.

Example 5—Determination of Molecular Weight

A Viscotek TDAmax temperature controlled, multi-detector SEC system comprising high sensitivity detectors in series—Photodiode Array UV, Light Scattering (both RALS and LALS), Refractive Index and Viscometer was used for the measurements. The refractive index detector recorded the concentration of the sample resulting in the respective distribution curve. In combination with the light scattering detectors, the molecular weight (MW) was determined. For size exclusion chromatography (SEC) analysis, samples were diluted with PBS resulting in a final polymer concentration of 0.1 mg/mL.

Errors or fluctuations which occur during this test typically result in a deviation of about 10%.

Example 6—Measurement of Extrusion Force

A 27G or a 30G needle was attached to a 1 mL syringe containing the hydrogel composition. The extrusion force was measured with a Mecmesin force testing system and an extrusion rate of 12 mm/min. Measurements were performed at least in duplicate. The calculated mean extrusion force (EF) for the investigated hydrogel composition is indicated.

Example 7—Preparation and Characterisation of a Hydrogel Composition Comprising 7 mg/mL Crosslinked Hyaluronan-Lysyl-Cysteamine A hydrogel comprising 0.7% crosslinked hyaluronan-lysyl-cysteamine sodium salt (HA-LYSC) and 0.3% unmodified sodium hyaluronate was produced according to method B without addition of lidocaine HCl. In brief, 525 mg HA-LYSC (dry weight, MMW 590 kDa, degree of modification 149 µmol/g polymer) and 225 mg sodium hyaluronate (dry weight, MMW 2.4 MDa) were dissolved in 66.2 g 0.01 M HCl (comprising 540 mg NaCl) under mechanical stirring at room temperature for about 3 h. To 62.33 g of this solution, 6.925 ml 100 mM phosphate buffer pH 11.74, containing 0.018% $H_2O_2$ was added, which resulted in an adjustment of the pH of the solution to about pH 7.2. The mixture was left for 66h at 5° C. for crosslinking, then pressed through a 200 µm sieve, filled into 1 mL glass syringes and sterilized via autoclavation. The sterile hydrogel had a pH of about 7.1 and an osmolality of 309 mOsm/kg.

Degree of modification (DoM), MMW, residual thiol content, elastic modulus G', and extrusion force were determined as described above and are summarized in Table 1. For the measurement of extrusion force a 30G needle was attached to the syringe. For the determination of elastic modulus G' the hydrogel was applied to the rheometer directly from the syringe (without needle attachment).

TABLE 1

| | Characteristics of a hydrogel composition | | | | |
|---|---|---|---|---|---|
| ID | MMW HA-SH raw material [kDa] | DoM HA-SH raw material [µmol/g] | Elastic modulus G' (no needle) [mPa] | Residual thiol content [µmol/g] | Extrusion force [N] |
| INVENT 1 | 590 | 149 | 79,067 | 0 | 5 (30 G) |

Example 8—Preparation and Characterisation of a Hydrogel Composition Comprising 17.9 mg/mL Crosslinked Hyaluronan-Lysyl-Cysteamine A hydrogel comprising 1.79% crosslinked hyaluronan-lysyl-cysteamine sodium salt (HA-LYSC) and 0.5% unmodified sodium hyaluronate was produced according to method B without addition of lidocaine HCl. In brief, 1.34 g HA-LYSC (dry weight, MMW 590 kDa, degree of modification 149 µmol/g polymer) and 375 mg sodium hyaluronate (dry weight, MMW 2.4 MDa) were dissolved in 65.2 g 0.01 M HCl (comprising 458 mg NaCl) under mechanical stirring at room temperature for about 4 h. To 62.30 g of this solution, 6.92 ml 100 mM phosphate buffer pH11.90, containing 0.045% $H_2O_2$ was added, which resulted in an adjustment of the pH of the solution to about pH 7.2. The mixture was left for 66h at 5° C. for crosslinking, then pressed through a 200 μm sieve, filled into 1 mL glass syringes and sterilized via autoclavation. The sterile hydrogel had a pH of about 7.2 and an osmolality of 303 mOsm/kg.

Degree of modification (DoM), MMW, residual thiol content, elastic modulus G' and extrusion force were determined as described above and are summarized in Table 2. For the measurement of extrusion force a 27G needle was attached to the syringe. For the determination of elastic modulus G' the hydrogel was applied to the rheometer directly from the syringe (without needle attachment).

TABLE 2

Characteristics of a hydrogel composition

| ID | MMW HA-SH raw material [kDa] | DoM HA-SH raw material [μmol/g] | Elastic modulus G' (no needle) [mPa] | Residual thiol content [μmol/g] | Extrusion force [N] |
| --- | --- | --- | --- | --- | --- |
| INVENT2 | 590 | 149 | 636,177 | 0 | 8 (27 G) |

Example 9—Preparation and Characterisation of a Hydrogel Composition Comprising 9 mg/mL Crosslinked Hyaluronan-Lysyl-Cysteamine A hydrogel comprising 9 mg/mL crosslinked hyaluronan-lysyl-cysteamine sodium salt (HA-LYSC) (and 3 mg/mL unmodified sodium hyaluronate was produced according to method B without addition of lidocaine HCl. In brief, 450 mg HA-LYSC (dry weight, MMW 505 kDa, degree of modification 158 μmol/g polymer) and 150 mg sodium hyaluronate (dry weight, MMW 2.4 MDa) were dissolved in 44 g 0.01 M HCl (comprising NaCl) under mechanical stirring at room temperature for about 5 hours. To 39.82 g of this solution, were added 4.425 mL of 100 mM phosphate buffer pH 12, containing 0.024% $H_2O_2$, which resulted in an adjustment of the pH to about pH 7.4. The mixture was homogenized for 15 min at ambient temperature and then left over night to complete crosslinking. The crosslinked gel was filled into 1 mL glass syringes and sterilized via autoclavation. The sterilized gel had a pH of about 7.5 and an osmolality of 315 mOsmol/kg.

Degree of modification (DoM), MMW, residual thiol content, and elastic modulus G' were determined as described above and are summarized in Table 3. For the determination of elastic modulus G' the hydrogel was applied to the rheometer directly from the syringe (without needle attachment).

TABLE 3

Characteristics of a hydrogel composition

| ID | MMW HA-SH raw material [kDa] | DoM HA-SH raw material [μmol/g] | Residual thiol content [μmol/g] | Elastic modulus G' [mPa] |
| --- | --- | --- | --- | --- |
| INVENT3 | 505 | 158 | 0 | 248,863 |

Example 10—Preparation and Characterisation of a Hydrogel Composition Comprising 35 mg/mL Crosslinked Hyaluronan-Lysyl-Cysteamine A hydrogel comprising 35 mg/mL crosslinked hyaluronan-lysyl-cysteamine sodium salt (HA-LYSC) and 3 mg/mL unmodified sodium hyaluronate was produced according to method B without addition of lidocaine HCl. In brief, 700 mg HA-LYSC (dry weight, MMW 590 kDa, degree of modification 149 μmol/g polymer) and 60 mg sodium hyaluronate (dry weight, MMW 2.4 MDa) were dissolved in 17 g 0.01 M HCl (comprising NaCl) under mechanical stirring at room temperature for about 5 hours. To 16.28 g of this solution 1.81 ml of 100 mM phosphate buffer pH 12 containing 0.089% $H_2O_2$ were added, which resulted in an adjustment of the pH of the solution to about pH 7.1. The mixture was homogenized for 15 min and then left for 18 h at room temperature to complete crosslinking. The crosslinked gel was filled into 1 mL glass syringes and sterilized via autoclavation. The sterilized gel had a pH of about 7.0 and an osmolality of 334 mOsmol/kg.

Degree of modification (DoM), MMW, residual thiol content, elastic modulus G', and extrusion force were determined as described above and are summarized in Table 4. For the measurement of extrusion force a 27G needle was attached to the syringe. For the determination of elastic modulus G' the hydrogel was applied to the rheometer directly from the syringe (without needle attachment).

TABLE 4

Characteristics of a hydrogel composition

| ID | MMW HA-SH raw material [kDa] | DoM HA-SH raw material [μmol/g] | Residual thiol content [μmol/g] | Elastic modulus G' [mPa] | Extrusion force [N] |
| --- | --- | --- | --- | --- | --- |
| INVENT4 | 590 | 149 | 0 | 1 939 050 | 27 |

Example 11—Comparison of Various Sterile Hydrogel Compositions

Various compositions and their characteristics are listed in Table 5. The main differences of the comparative compositions ID 1 to ID 8 are the concentration and the molecular weight characteristics of the crosslinked polymer, which is an oxidation product of HA-cysteamine. Hydrogel compositions INVENT1 and INVENT2 were prepared by crosslinking HA-lysyl-cysteamine. Sterile hydrogel compositions comprising crosslinked thiol-modified hyaluronan, unmodified sodium hyaluronate and 3 mg/mL lidocaine HCl were produced with similar methods (compare methods A, B and I above).

Hydrogel compositions ID 1 to ID 4 were produced with a hyaluronan-cysteamine polymer with a MMW of 150 kDa and a degree of modification of 118 μmol/g. Hydrogel compositions ID 1 to ID 3 comprised 3 mg/mL unmodified sodium hyaluronate and 6 mg/mL (ID 1), 9 mg/mL (ID 2) and 13 mg/mL (ID3) crosslinked hyaluronan-cysteamine, respectively. Hydrogel composition ID 4 comprised 4 mg/mL unmodified sodium hyaluronate and 13 mg/mL crosslinked hyaluronan-cysteamine.

Hydrogel compositions ID 5 and ID 6 were produced with a hyaluronan-cysteamine polymer with a MMW of 730 kDa and a degree of modification of 151 μmol/g. Hydrogels ID 5 and ID 6 comprised 3 mg/mL unmodified sodium hyaluronate (MMW 2.41 MDa) and 5 mg/mL (ID 5) and 9 mg/mL (ID 6) crosslinked hyaluronan-cysteamine sodium salt, respectively.

Hydrogel compositions ID 7 and ID 8 were produced with a hyaluronan-cysteamine polymer with a MMW of 780 KDa and a degree of modification of 149 μmol/g. Hydrogel composition ID 7 comprised 3 mg/ml unmodified sodium hyaluronate (MMW 1.94 MDa), and 7 mg/ml crosslinked hyaluronan-cysteamine sodium salt. Hydrogel composition ID 8 comprised 3 mg/ml unmodified sodium hyaluronate (MMW 1.94 MDa), and 13 mg/ml crosslinked hyaluronan-cysteamine sodium salt.

Hydrogel composition ID 9 was produced according to method B with a hyaluronan-cysteamin polymer with a MMW of 720 kDa and a degree of modification of 146 μmol/g. Hydrogel composition ID 9 comprised 3 mg/ml unmodified sodium hyaluronate (MMW 1.94 MDa) and 17.9 mg/ml crosslinked hyaluronan-cysteamine sodium salt.

Hydrogel compositions INVENT1 (Example 7) and INVENT2 (Example 8) were produced with a hyaluronan-lysyl-cysteamine polymer with a MMW of 590 kDa and a degree of modification of 149 μmol/g. Hydrogel composition INVENT1 comprised 3 mg/ml unmodified sodium hyaluronate (MMW 1.94 MDa), and 7 mg/ml crosslinked hyaluronan-lysyl-cysteamine sodium salt. Hydrogel composition INVENT2 comprised 5 mg/ml unmodified sodium hyaluronate (MMW 1.94 MDa), and 17.9 mg/ml crosslinked hyaluronan-lysyl-cysteamine sodium salt.

The thiol-modified hyaluronan MMW and its degree of modification (DoM), the elastic modulus G' and the extrusion force (EF) of the sterile hydrogel composition, and residual thiol content of crosslinked polymer in the sterile hydrogel composition were determined as described above.

All sterile hydrogel compositions had a pH in the range of 6.7 to 7.8 and an osmolality in the range of 250 to 350 mOsm/kg It was surprisingly found that the elastic properties of the hydrogels were not only influenced by the concentration of the crosslinked polymer but also by the MMW and the addition of lysine to the thiol bearing modification agent of the thiol-modified hyaluronan.

Comparison of the elastic modulus of hydrogel composition ID 3* and ID 8* shows that the MMW of the thiol-modified hyaluronan used for crosslinking had a positive influence on the elastic properties of the sterile composition. The thiol-modified hyaluronan of hydrogel composition ID 3* had a MMW of 150 kDa, whereas the thiol-modified hyaluronan of hydrogel composition ID 8* had a MMW of 780 kDa. Other than that, both hydrogel compositions comprised 13 mg/ml crosslinked hyaluronan-cysteamine, 3 mg/ml unmodified sodium hyaluronate and 3 mg/ml lidocaine HCl, and both hydrogel compositions were produced by the same production method.

Comparison of the elastic modulus of hydrogel composition ID 7* and INVENT1 shows that compositions comprising crosslinked hyaluronan-lysyl-cysteamine are less elastic than compositions comprising crosslinked hyaluronan-cysteamine. Both hydrogel compositions comprised 7 mg/ml crosslinked thiol modified hyaluronan, 3 mg/ml unmodified sodium hyaluronate and 3 mg/ml lidocaine HCl, and both hydrogel compositions were produced by the same production method (B). The same effect was seen when comparing the elastic modulus of hydrogel compositions ID 9* and INVENT2.

Example 12—In Vivo Characterization of Implanted Hydrogel Compositions

Various compositions according to the invention as well as comparative compositions were investigated for the development of the mean depot volume over time after intradermal implantation via injection with magnetic resonance imaging (MRI).

TABLE 5

Characteristics of sterile hydrogel compositions comprising crosslinked polymers

| Hydrogel composition | HA-SH Polymer MMW kDa | Elastic modulus G' mPa | EF N | DoM μmol/g | Residual thiol content μmol/g | Production method |
|---|---|---|---|---|---|---|
| ID 1* | 150 | 33,987 | 6 (30 G) | 118 | 0 | B |
| ID 2* | 150 | 140,218 | 11 (30 G) | 118 | 0 | B |
| ID 3* | 150 | 475,046 | 25 (30 G) | 118 | n.d. | B |
| ID 4* | 150 | 258,226 | 15 (30 G) | 118 | n.d. | I |
| ID 5* | 730 | 88,290 | 5 (30 G) | 151 | 0 | A |
| ID 6* | 730 | 390,540 | 10 (30 G) | 151 | 0 | A |
| ID 7* | 780 | 183,557$^a$ | 5 (30 G) | 149 | 1 | B |
| ID 8* | 780 | 817,850$^a$ | n.d. | 149 | 2 | B |
| ID 9* | 720 | 1,549,000$^a$ | 12 (27 G) | 146 | 3 | B |
| INVENT1 | 590 | 79,067 | 5 (30 G) | 149 | 0 | B $^b$ |
| INVENT2 | 590 | 636,177 | 8 (27 G) | 149 | 0 | B $^b$ |

An asterisk (*) indicates those examples that do not fall under the scope of the claims but are included for comparison. The abbreviation n.d. stands for "not determined".
$^a$For the determination of elastic modulus G' the hydrogel composition was applied to the rheometer directly from the syringe (without needle attachment).
$^b$ without lidocaine HCl The formation of disulfide bonds was monitored via measuring residual thiol content of the crosslinked polymers and comparison with the initial degree of modification of the thiol-modified hyaluronan. It was found that all hydrogel compositions according to this invention had a residual thiol content of less than 15% in respect to the degree of modification of the thiol-modified hyaluronan.

In detail, the depot volume in % relative to the starting point is calculated to compensate for potential differences in the application volume. The depot volume at t=0 (directly after implantation) corresponds to 100%. The depot volume may be monitored for example via magnet resonance imaging (MRI) scans.

It will be understood that the depot volume as biological parameter, preferably determined in animal models, is subject to great individual variation. Accordingly individual data points are less informative and only mean values (considering multiple application sites and/or multiple study objects) give conclusive data. Of course, the performance will further depend on factors such as the tissue type at the site of implantation, the used method for measuring the depot volume and the species of the studied organism. The quantitative transferability of the data, e.g. for application in humans, may be restricted. However, results comparable to the data in rats were observed in another in vivo study with mice (data not shown). Thus, the in vivo characterisation provides a valuable tool for assessing and comparing individual hydrogel compositions against each other.

Residence time may be used as a parameter to describe the presence of a mean depot volume during a period of time, preferably the presence of a depot volume of about 100% (or even greater) during a time period. A volumizing effect may be defined by a depot volume of about 100% (or greater) at a certain time point after the application of the hydrogel, for example measured in week 5 (e.g. at day 30) or in another embodiment, in week 12 (e.g. at day 81 to 84), and eventually even in week 24 (e.g. measured at 165 to 168 days) post-implantation.

Eleven different sterile hydrogel compositions (see Table 6 for hydrogel characteristics) and two commercially available dermal fillers for fine line treatment, Belotero® soft (COMP1) and Profhilo® (COMP2), were tested. COMP1 contains 20 mg/mL BDDE crosslinked hyaluronan and 3 mg/mL lidocaine HCl in a phosphate buffered solution. COMP2 contains 16 mg/mL high MW hyaluronan and 16 mg/mL low MW hyaluronan in a phosphate buffered solution.

The compositions were injected intradermally into the back skin of female Sprague Dawley rats. The injection volume was about 50 µL. A maximum of 8 depots was applied per rat with a total of 12 applications per composition ID 5, ID 6, ID 7, ID 8 and ID 9, 14 applications per composition ID 1, ID 2 and COMP1, 5 applications per composition ID 3 and ID 4, 16 applications per INVENT1 and INVENT2 and 8 applications per COMP2. The volume of the intradermal hydrogel depots was monitored by MRI (Siemens Espree 1.5 T MRT device) at distinct time points for a total time period of up to 170 days. Individual depot volumes (mm$^3$) were calculated according to MRI scans and monitored over time. Calculated volumes were normalized to results obtained at Day 0 (immediately after application) and are indicated in percent (%). The mean relative depot volumes of different compositions at different time points are listed in Table 6. A certain range of days was allowed for each time point. For each hydrogel compositions, all depot volumes were determined on the same day.

TABLE 6

Development of the mean relative depot volume (%) over time

| | Mean relative depot volume (%) | | | | | | | | |
|---|---|---|---|---|---|---|---|---|---|
| Hydrogel composition | Day 7 | Day 14 | Day 21-24 | Day 28-30 | Day 53-56 | Day 81-84 | Day 107-112 | Day 133-140 | Day 168-170 |
| ID 1* | 14.1 | 0.0 | 0.0 | n.d. | n.d. | n.d. | n.d. | n.d. | n.d. |
| ID 2* | 27.3 | 6.9 | 0.0 | n.d. | n.d. | n.d. | n.d. | n.d. | n.d. |
| ID 3* | n.d. | n.d. | n.d. | 15.9 | 4.7 | n.d. | n.d. | n.d. | n.d. |
| ID 4* | n.d. | n.d. | n.d. | 10.1 | 0.0 | n.d. | n.d. | n.d. | n.d. |
| ID 5* | n.d. | n.d. | 67.6 | n.d. | 54.9 | 49.2 | 48.3 | 41.5 | 39.5 |
| ID 6* | n.d. | n.d. | 108.1 | n.d. | 85.7 | 85.7 | 75.8 | 75.3 | 75.9 |
| ID 7* | n.d. | n.d. | n.d. | 93.2 | 93.1 | 77.4 | 75.0 | 67.8 | 63.6 |
| ID 8* | n.d. | n.d. | n.d. | 136.7 | 114.1 | 103.7 | 98.0 | 94.5 | 85.2 |
| COMP1* | 5.2 | 0.0 | 0.0 | n.d. | n.d. | n.d. | n.d. | n.d. | n.d. |
| COMP2* | n.d. | n.d. | 0.0 | n.d. | 0.0 | 0.0 | 0.0 | 0.0 | 0.0 |
| INVENT1 | 58.1 | 48.1 | n.d. | 34.3 | 14.8 | 7.6 | 1.7 | 2.0 | 1.6 |
| INVENT2 | 145.3 | 145.8 | n.d. | 123.5 | 86.1 | 75.11 | 62.1 | 55.9 | 49.5 |
| ID 9* | 130.9 | 149.4 | n.d. | 148.9 | 137.6 | 125.0 | 123.2 | 115.6 | 105.6 |

An asterisk (*) indicates those examples that do not fall under the scope of the claims but are included for comparison. The abbreviation n.d. stands for "not determined".

Comparative hydrogel compositions ID 1* to ID 4*, as well as COMP1 and COMP2, were degraded very quickly within less than 2 months after application. In some cases, hydrogel depots were not detectable 2 weeks (COMP1 and composition ID 1*) and about 3 weeks (COMP2 and composition ID 2*) after implantation. Hydrogel compositions ID 5*, ID 6*, ID 7* and ID 8*, which were prepared by crosslinking thiol-modified hyaluronan with an initial MMW in the range of 730 to 780 kDa, showed a prolonged residence time of more than 1 month and up to 5 months. Comparison of the residence time of hydrogel composition ID 3* and ID 8* shows that the MMW of the thiol-modified hyaluronan used for crosslinking had a positive influence on the residence time of the sterile composition. The thiol-modified hyaluronan of hydrogel composition ID 3* had a MMW of 150 kDa and depots of hydrogel composition ID 3* were not detectable 3 months after implantation. The thiol-modified hyaluronan of composition ID 8* had a MMW of 780 kDa and depots of hydrogel composition ID 8* were detected during the entire study period. Both hydrogel compositions were otherwise comparable; they comprised 13 mg/ml crosslinked hyaluronan-cysteamine, 3 mg/ml unmodified sodium hyaluronate and 3 mg/ml lidocaine HCl, and both compositions were produced by the same production method.

Comparison of the mean relative depot volume of hydrogel composition ID 7* and INVENT1 shows that the composition comprising crosslinked hyaluronan-lysyl-cysteamine at a relatively low concentration of 7 mg/ml shows a faster mean depot volume decrease than the composition comprising crosslinked hyaluronan-cysteamine at the same concentration. Both hydrogel compositions comprised 7 mg/ml crosslinked thiol modified hyaluronan and 3 mg/ml unmodified sodium hyaluronate, and both hydrogel compositions were produced by the same production method (B).

The same observation was made when comparing a hydrogel composition comprising crosslinked hyaluronan-lysyl-cysteamine (INVENT2) in a concentration of 17.9 mg/ml with hydrogel compositions comprising crosslinked hyaluronan-cysteamine in the same concentration of 17.9 mg/ml (ID 9*). After 24 weeks the mean relative depot volume of hydrogel composition INVENT2 was about 50%.

The hydrogel compositions according to invention show the desired in vivo performance promising for an applicability as biodegradable soft tissue filler, e.g. in humans. Moreover, the nature of the crosslinked polymer provides a favourable toxicological safety profile and higher volumes as compared with other stabilized hyaluronan fillers may be applied (above 50 mL per application).

Example 13—Biocompatibility Studies on Implanted Hydrogel Compositions

In order to study the biocompatibility of the compositions, samples from hydrogel implantation sites implanted hydrogels were investigated histologically.

Hematoxylin and eosin (H&E) stained tissue sections were prepared from the implantation sites of two different hydrogels of the invention (INVENT1 and INVENT2) 28 days post-implantation. The histological evaluation revealed that the implants were located in dermal (intradermal; i.d.), muscle (intramuscular; i.m.) or subcutaneous (subcutaneous; s.c.) tissues.

Qualitatively, at all implantation sites examined, the implanted material (test item) presented itself as a slightly bluish, homogeneously staining, amorphous mass forming a network within dermal, muscular or subcutaneous tissues. The local host reactions can be described in terms of varying degree of infiltration of polymorphonuclear cells, lymphocytes and/or macrophages with/without multinucleated giant cells, as well as fibrosis (including proliferation of fibroblasts or fibrocytes). The local host reactions were slightly more remarkable at the s.c. site compared to that at the i.d. and i.m. sites, although the overall reactions were qualitatively not different between locations. There were no unexpected host reactions in any implantation sites examined under the conditions of this experiment.

For quantifying the effects at the implantation sites, a scoring system described by ISO 10993-6:2016(E) was applied, wherein a higher score indicates a more pronounced host reaction. Based on the host reaction scores determined according to adapted ISO 10993-6:2016(E) scoring system, composition INVENT1 had a mean host reaction score for combined tissues (i.d., i.m. and s.c.) of 9.6 and composition INVENT2 had a mean host reaction score of 12.3.

Under the conditions of this study, the hydrogel implants of composition INVENT2 comprising hyaluronan-lysyl-cysteamin in a 2.5-fold higher concentration were considered to demonstrate minimal or no difference in reaction to the tissue as compared to the hydrogel implants of composition INVENT1.

Example 14—Rheological Characterization of Different Thiol-Modified Hyaluronans Three different thiol-modified hyaluronans were produced using different thiol group-bearing modification agents. The modification agent for the HA-lysyl-cysteamine was prepared according to example 15 A (see below). The HA-cysteamine was prepared as described before and the DGDTPDH modification agent was prepared according to PCT/EP2019/065755, example 12 incorporated herein by reference.

The rheological properties of the thiol-modified hyaluronans in solution (without prior crosslinking) were evaluated. First, a 1.2% (m/m) solution of the thiol-modified hyaluronan was prepared in 0.01N HCl by continuous stirring for 2 to 4 hours, followed by filtration (10 µm). Dynamic viscosity was determined within 30 min after filtration using an Anton Paar MCR 102 Rheometer with a cone-plate system at a temperature of 25° C. and a constant shear rate of 5/s.

TABLE 7

Dynamic viscosity of solutions of different thiol-modified hyaluronans

| Thiol-modified hyaluronan | MMW HA-SH raw material [kDa] | DoM HA-SH raw material [µmol/g] | Viscosity 1.2% solution share rate 5 s$^{-1}$ [mPa * s] |
|---|---|---|---|
| Hyaluronan-cysteamine | 730 | 150 | 961 |
| HADGDTPH | 767 | 134 | 814 |
| Hyaluronan-lysyl cysteamine | 500 | 210 | 124 |
| Hyaluronan-lysyl cysteamine | 500 | 158 | 114 |
| Hyaluronan-lysyl cysteamine | 590 | 149 | 273 |

Example 15—Synthesis of Thiol Group Bearing Modification Agents with Basic Side Chain

A. Preparation of bis(Lysyl)-cystamine dihydrochloride

To a mixture of cystamine dihydrochloride (842 mg, 3.74 mmol) and diisopropylethylamine (DIPEA, 1.36 mL, 7.85 mmol) in dry THF (10 mL) was added dropwise a solution of $N_\alpha, N_\epsilon$-Di-Boc-L-lysine hydroxysuccinimide ester (3.32 g, 7.48 mmol) in dry THF (10 mL). The reaction was stirred for 18 h at ambient temperature, then another 0.7 mL of DIPEA, followed by water (1 mL) were added and stirring was continued for 24 h.

The mixture was poured on 200 mL water and extracted with ethyl acetate (500 mL). The organic layer was washed with 1 n HCl (100 mL), half saturated NaHCO$_3$ (100 mL) and water (50 mL), then dried over Na$_2$SO$_4$ and volatiles were evaporated under reduced pressure to give the N-Boc protected bis(Lysyl)-cystamine as a colourless foam.

Yield: 2.2 g (73%). $^1$H NMR (400 MHz, CDCl$_3$) δ 7.11 (br, 1H, —NH), 5.53 (br, 1H, —NH), 4.74 (br, 1H, —NH), 4.15 (br, 1H, α-$\underline{CH}$—NH), 3.70-3.45 (m, 2H, $\underline{CH_2}$—NH—), 3.17-3.03 (m, $\overline{2H}$, ε-$\underline{CH_2}$—NH), 2.80 (t, J=6.6 Hz, 2H, —$\underline{CH_2}$—S—), 1.94-1.$\overline{21}$ (m, 24H, β, γ, δ-$\underline{CH_2}$, 2×t-Bu), 1.77-1.67 (m, 2H, —$\underline{CH_2}$), 1.52-1.42 (m, $\overline{2H}$, —$\underline{CH_2}$). m/z=809.4 [M+H]$^+$, 831.3 [M+Na]$^+$.

To a solution of the N-protected bis(Lysyl)-cystamine (1.03 g, 1.273 mmol) in MeOH (25 mL) was added acetyl chloride (500 µL, 7 mmol). The reaction was stirred in a flask equipped with a reflux condenser for 5 h at 70° C., then volatiles were evaporated under reduced pressure and residual hydrochloric acid was removed by co evaporation with toluene (2×mL). The crude product was taken up in water (10 mL), washed with toluene (5 mL) and the aqueous layer was lyophilized to give the title compound as a colourless foam.

Yield: 669 mg (95%). $^1$H NMR (400 MHz, D$_2$O) δ 3.99 (t, J=6.3 Hz, 1H, α-C$\underline{H}$—NH$_3$), 3.72-3.62 (m, 1H, —NH—C$\underline{H}_{2A}$), 3.59-3.50 (m, 1H, —NH—C$\underline{H}_{2B}$), 3.01 (t, J=8.0 Hz, 2H, ε-C$\underline{H}_2$—NH$_3$), 2.97-2.83 (m, 2H, —C$\underline{H}_2$—S—), 1.97-1.87 (m, 2H, β-C$\underline{H}_2$), 1.77-1.67 (m, 2H, δ-C$\underline{H}_2$), 1.52-1.42 (m, 2H, γ-C$\underline{H}_2$).

B. Preparation of bis(epsilon-azido-L-lysinyl)-cystamine dihydrochloride

To a mixture of cystamine dihydrochloride (591 mg, 2.62 mmol) and N-alpha-t-Butyloxycarbonyl-epsilon-azido-L-lysine (1.5 g, 5.50 mmol) in dry dichloromethane:DMF=1:1 (20 mL), DIPEA (914 µL, 5.25 mmol) was added, followed by a solution of EDC*HCl (1.06 g, 5.50 mmol) in dichloromethane under ice cooling over a period of 15 min. The reaction was stirred for 5 days at ambient temperature; then volatiles were evaporated under reduced pressure. The residue was taken up in ethyl acetate (150 mL) and washed with 1 N HCl (50 mL) and subsequently with half saturated NaHCO$_3$ (50 mL). The organic layer was dried over Na$_2$SO$_4$ and volatiles were evaporated under reduced pressure. The crude product was purified via flash chromatography on silica: Cyclohexane/Ethyl acetate=70:30 to 50:50. The compound was obtained as colorless oil that crystallized upon standing.

Yield: 125 mg (7%). $^1$H NMR (400 MHz, CDCl$_3$) δ 7.20 (br, 1H, NH), 5.54 (br, 1H, NH), 4.21 (br, 1H, α-C$\underline{H}$), 3.74-3.43 (m, 2H, —C$\underline{H}_2$—NH—), 3.28 (t, J=6.8 Hz, 2H, ε-C$\underline{H}_2$—N$_3$), 2.80 (at, J=6.3 Hz, 2H, C$\underline{H}_2$—S), 1.9-1.39 (m, 15H, —CH$_2$, C$\underline{H}_3$ t-Bu). m/z=661.3 [M+H]$^+$, 683.3 [M+Na]$^+$.

To a solution of prepared bis(N-alpha-t-Butyloxycarbonyl-epsilon-azido-L-lysinyl)-cystamine (256 mg, 0.39 mmol) in MeOH (5 mL) acetylchloride (250 µL, 3.5 mmol) was added. The reaction was stirred in a flask equipped with a reflux condenser for 3 h at 70° C.; then volatiles were evaporated under reduced pressure. The crude product was taken up in water (15 mL), washed with EtOAc (5 mL), and the aqueous layer was lyophilized to give compound (12) as a colorless foam.

Yield: 174 mg (84%). $^1$H NMR (400 MHz, D$_2$O) δ 3.97 (t, J=6.6 Hz, 1H, α-C$\underline{H}$—NH$_3$), 3.75 (ddd, J$_{gem}$=14.1 Hz J$_{vic1}$=7.4 Hz, J$_{vic2}$=5.5 Hz, 1H, —NH—C$\underline{H}_{2A}$), 3.48 (dt, J$_{vic}$=5.8 Hz 1H, —NH-C$\underline{H}_{2B}$), 3.35 (t, J=6.6 Hz, 2H, ε-C$\underline{H}_2$—NH$_3$), 2.97-2.81 (m, 2H, —C$\underline{H}_2$—S—), 1.95-1.85 (m, 2H, β-C$\underline{H}_2$), 1.69-1.59 (m, 2H, δ-C$\underline{H}_2$), 1.55-1.38 (m, 2H, γ-C$\underline{H}_2$). m/z=461.2 [M+H]$^+$, 483.2 [M+Na]$^+$.

Example 16—Determination of the Binding Modality of a Lysine Modification Group in Thiol-Modified Hyaluronan As lysine has two amino groups, two alternative binding modalities are possible for amide coupling with the carboxylate of the hyaluronan (i.e. substructure according to formula (I) or formula (II) as discussed above). The binding modality can be determined by means of $^1$H and $^{13}$C-NMR as well as combined 2D NMR techniques (HSQC, HMBC).

CH$_2$ groups adjacent to alpha or epsilon amino groups in synthesized lysine derivatives can be clearly distinguished by different chemical shifts in $^1$H-NMR spectra. If the amino groups are acylated, the signal of the adjacent —CH$_2$ groups are shifted downfield in the order of 0.1-0.2 ppm due to the electron withdrawing acyl moiety. In the free bis(Lysyl)-cystamine, the signals for alpha amino groups are found at δ=3.99 ppm and the signals epsilon amino groups are found at δ=3.01 ppm. In a derivate, wherein both amino groups are protected by BOC (t-Butoxycarbonyl), these signals shift to 4.15 ppm and to 3.10 ppm, respectively.

A similar downfield shift is also found for corresponding $^{13}$C signals (alpha-CH group: δ=53.19 to 54.40 ppm; epsilon-CH$_2$ group: δ=39.06 to 40.09 ppm).

The HSQC spectrum of the thiol-modified hyaluronan hyaluronan-lysyl-cysteamine used for the preparation of hydrogel compositions INVENT1, INVENT2 and INVENT4 showed a $^1$H/$^{13}$C crosspeak for the alpha-CH group of δ=4.24/57.45 ppm, whereas the epsilon-CH$_2$ group was found at δ=3.00/41.62 ppm. A downfield shift was found for the alpha-CH group but not for the epsilon-CH$_2$ group. Thus, the NMR data indicate that the lysine linker was bound via the alpha-CH group to the hyaluronan and not via the epsilon-CH$_2$ group.

The invention claimed is:

1. A thiol-modified hyaluronan, wherein the thiol-modified hyaluronan comprises a plurality of modification groups with a thiol-group in the hyaluronan side-chains, wherein the modification group comprises an amino acid residue with a basic side chain and a conjugated terminal naturally occurring amino-thiol.

2. The thiol-modified hyaluronan according to claim 1, wherein the modification group is linked to the hyaluronan via a carboxamide, wherein the acyl group of the carboxamide originates from the carboxyl group of the glucuronic acid moiety in the hyaluronan.

3. The thiol-modified hyaluronan according to claim 1, wherein the amino group of the amino-thiol is conjugated to the carboxyl group of the amino acid residue to form a carboxamide.

4. The thiol-modified hyaluronan according to claim 1, wherein the modification group comprises an amino acid residue derived from the amino acid lysine and the amino-thiol cysteamine, wherein the amino group of the cysteamine is conjugated to the carboxyl group of the lysine.

5. The thiol-modified hyaluronan according to claim 1, wherein the thiol-modified hyaluronan has substructure according to formula (I) or formula (II) or both;

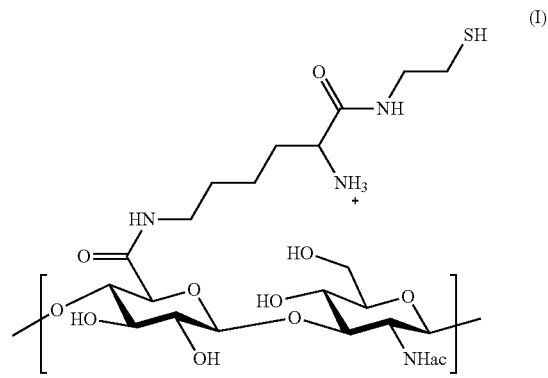

(I)

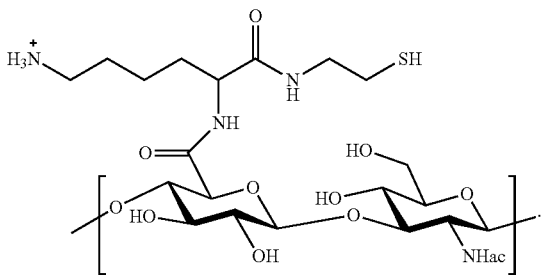

(II)

6. The thiol-modified hyaluronan according to claim 1, wherein;
the thiol-modified hyaluronan has a degree of modification with thiol groups of more than about 80 μmol per gram polymer, and
the thiol-modified hyaluronan has a degree of modification with thiol groups of less than about 320 μmol per gram polymer.

7. The thiol-modified hyaluronan according to claim 1, wherein the thiol-modified hyaluronan has a mean molecular weight of at least 400 kDa.

8. The thiol-modified hyaluronan according to claim 1, wherein the conjugated terminal naturally occurring aminothiol is selected from the group consisting of cysteamine, cysteine, homocysteine, esters of cysteine, and esters of homocysteine.

9. The thiol-modified hyaluronan according to claim 2, wherein the amino group of the carboxamide originates from an amino group of the amino acid residue.

10. The thiol-modified hyaluronan according to claim 6, wherein:
the thiol-modified hyaluronan has a degree of modification with thiol groups of more than about 105 μmol per gram polymer, or more than about 120 μmol per gram polymer, and the thiol-modified hyaluronan has a degree of modification with thiol groups of less than about 290 μmol per gram polymer, or less than 250 μmol per gram polymer.

11. The thiol-modified hyaluronan according to claim 7, wherein the thiol-modified hyaluronan has a mean molecular weight of at least 500 kDa, or at least 600 kDa.

12. A sterile hydrogel composition comprising a crosslinked polymer, wherein the crosslinked polymer is an oxidation product of a thiol-modified hyaluronan according to claim 1.

13. The sterile hydrogel composition according to claim 12, wherein the composition has a residual thiol content of less than 20% in respect to the degree of modification of the thiol-modified hyaluronan.

14. The sterile hydrogel composition according to claim 12, wherein the thiol-modified hyaluronan is comprised in the composition with a concentration of at most 50 mg/mL.

15. The sterile hydrogel composition according to claim 12, wherein the thiol-modified hyaluronan is comprised in the composition with a concentration of at least 4 mg/ml.

16. The sterile hydrogel composition according to claim 12, wherein the composition further comprises a local anaesthetic agent.

17. The sterile hydrogel composition according to claim 12, wherein the composition further comprises an unmodified polymer selected from a group of biocompatible polysaccharides.

18. The sterile hydrogel composition according to claim 14, wherein the thiol-modified hyaluronan is comprised in the composition with a concentration of at at most 35 mg/mL, or at most 25 mg/ml, or at most 18 mg/ml.

19. The sterile hydrogel composition according to claim 15, wherein the thiol-modified hyaluronan is comprised in the composition with a concentration of at least 5 mg/ml, or at least 7 mg/ml.

20. The sterile hydrogel composition according to claim 16, wherein the local anaesthetic agent is lidocaine.

21. The sterile hydrogel composition according to claim 17, wherein the unmodified polymer is an unmodified hyaluronan.

* * * * *